(12) United States Patent
Shai et al.

(10) Patent No.: US 7,671,011 B2
(45) Date of Patent: Mar. 2, 2010

(54) ANTIMICROBIAL AND ANTICANCER LIPOPEPTIDES

(75) Inventors: Yechiel Shai, Yehud (IL); Dorit Avrahami, Ashdod (IL)

(73) Assignee: Yeda Research & Development Co. Ltd., Rehovot (IL)

( * ) Notice: Subject to any disclaimer, the term of this patent is extended or adjusted under 35 U.S.C. 154(b) by 327 days.

(21) Appl. No.: 10/560,727

(22) PCT Filed: Jun. 18, 2004

(86) PCT No.: PCT/IL2004/000544

§ 371 (c)(1),
(2), (4) Date: Oct. 10, 2006

(87) PCT Pub. No.: WO2004/110341

PCT Pub. Date: Dec. 23, 2004

(65) Prior Publication Data

US 2007/0072808 A1 Mar. 29, 2007

Related U.S. Application Data

(60) Provisional application No. 60/479,465, filed on Jun. 19, 2003.

(51) Int. Cl.
*C07K 7/00* (2006.01)
(52) U.S. Cl. .............................. 514/2; 530/327; 530/328
(58) Field of Classification Search ...................... 514/2; 530/329, 330, 331, 327, 328
See application file for complete search history.

(56) References Cited

U.S. PATENT DOCUMENTS

| | | | | |
|---|---|---|---|---|
| 3,817,973 | A * | 6/1974 | Bouchaudon et al. ....... | 530/319 |
| 5,583,198 | A | 12/1996 | Whittaker ................... | 530/345 |
| 5,837,249 | A | 11/1998 | Heber-Katz et al. ...... | 424/186.1 |
| 5,871,746 | A | 2/1999 | Boutillon et al. .......... | 424/208.1 |
| 6,011,008 | A | 1/2000 | Domb et al. ................. | 514/8 |
| 6,011,013 | A | 1/2000 | Carr et al. .................... | 514/13 |
| 6,172,038 | B1 | 1/2001 | Shai et al. ...................... | 514/2 |
| 6,183,736 | B1 | 2/2001 | Moyne et al. .......... | 424/93.462 |
| 6,384,013 | B1 | 5/2002 | Burkhardt et al. ............ | 514/11 |
| 6,794,490 | B2 * | 9/2004 | Hill et al. ...................... | 530/317 |
| 7,262,268 | B2 * | 8/2007 | Morytko et al. ............. | 530/317 |
| 2002/0077317 | A1 | 6/2002 | Das ........................... | 514/171 |

FOREIGN PATENT DOCUMENTS

| WO | WO98/37090 | 8/1998 |
|---|---|---|
| WO | WO02/40529 | 5/2002 |

OTHER PUBLICATIONS

Creemer L. C. (J Med Chem. 39(25), 5021-4, 1996).*
Uehara Y (Journal of Antibiotics 29(9), 937-943, 1976).*
Schott H (Anti-Cancer Drug Design 11(6), 451-62, 1996).*
Trani A [Farmaco (Societa Chimica Italiana: 1989), 51(7), 503-512, 1996].*
Clark C. R. (J Med Chem. 30(7), 1214-18, 1987).*
Alexander et al., "Antifungal resistance trends towards the year 2000. Implications for therapy and new approaches". Drugs. Nov. 1997;54(5):657-78.
Avrahami et al., "Effect of multiple aliphatic amino acids substitutions on the structure, function, and mode of action of diastereomeric membrane active peptides". Biochemistry Oct. 23, 2001;40(42):12591-603.
Avrahami et al., "Conjugation of a magainin analogue with lipophilic acids controls hydrophobicity, solution assembly, and cell selectivity". Biochemistry Feb. 19, 2002; 41(7):2254-63.
Bechinger, "The structure, dynamics and orientation of antimicrobial peptides in membranes by multidimensional solid-state NMR spectroscopy". Biochim Biophys Acta. Dec. 15, 1999;1462(1-2):157-83.
Denning DW. "Epidemiology and pathogenesis of systemic fungal infections in the immunocompromised host". J Antimicrob Chemother. Oct. 1999;28 Suppl B:1-16.
Efron et al., "Direct interaction of dermaseptin S4 aminoheptanoyl derivative with intraerythrocytic malaria parasite leading to increased specific antiparasitic activity in culture". J Biol Chem. Jul. 5, 2002;277(27):24067-72. Epub Apr. 5, 2002.
Gavish et al., "Growth inhibition of prostate cancer xenografts by halofuginone". Prostate. May 1, 2002;51(2):73-83.
Groll et al., "Trends in the postmortem epidemiology of invasive fungal infections at a university hospital". J Infect. Jul. 1996;33(1):23-32.
Hong et al., "Structure and organization of hemolytic and nonhemolytic diastereomers of antimicrobial peptides in membranes". Biochemistry. Dec. 21, 1999;38(51):16963-73.
Merrifield, "Solid phase peptide synthesis". J. Am. Chem. Soc. Jan. 31, 1963; 85: 2149-2154.
Minamoto et al., "Fungal infections in patients with acquired immunodeficiency syndrome". Med Clin North Am. Mar. 1997;81(2):381-409.
Oren et al., "Selective lysis of bacteria but not mammalian cells by diastereomers of melittin: structure-function study". Biochemistry. Feb. 18, 1997;36(7):1826-35.
Oren et al., "A repertoire of novel antibacterial diastereomeric peptides with selective cytolytic activity". J Biol Chem. Jun. 6, 1997;272(23):14643-9.
Oren et al., "Mode of action of linear amphipathic alpha-helical antimicrobial peptides". Biopolymers. 1998;47(6):451-63.
Papo et al., "A novel lytic peptide composed of DL-amino acids selectively kills cancer cells in culture and in mice". J Biol Chem. Jun. 6, 2003;278(23):21018-23. Epub Mar. 19, 2003.

(Continued)

*Primary Examiner*—David Lukton
(74) *Attorney, Agent, or Firm*—Winston & Strawn LLP

(57) ABSTRACT

Lipophilic conjugates comprise a peptide coupled to a fatty acid The peptide comprises at least two positively charged amino acid residues; the peptide after conjugation to the fatty acid possessing antibacterial, antifungal, and/or anticancer activity higher than prior to conjugation. The lipophilic conjugates are suitable for treatment of infections caused by pathogenic organisms such as bacteria and fungi. The lipophilic conjugates are also suitable for sanitation, as disinfectants, or for food preservation.

14 Claims, 4 Drawing Sheets

OTHER PUBLICATIONS

Shai et al., "Diastereoisomers of cytolysins, a novel class of potent antibacterial peptides". J Biol Chem. Mar. 29, 1996;271(13):7305-8.

Tossi et al., "Amphipathic, alpha-helical antimicrobial peptides". Biopolymers. 2000;55(1):4-30.

Tsubery et al., "Structure-function studies of polymyxin B nonapeptide: implications to sensitization of gram-negative bacteria". J Med Chem. Aug. 10, 2000;43(16):3085-92.

Unger et al., "The effect of cyclization of magainin 2 and melittin analogues on structure, function, and model membrane interactions: implications to their mode of action". Biochemistry. May 29, 2001;40(21):6388-97.

Walsh et al., "Recent progress and current problems in treatment of invasive fungal infections in neutropenic patients". Infect Dis Clin North Am. Jun. 1996;10(2):365-400.

* cited by examiner

SEQUENCE LISTING

```
<160> NUMBER OF SEQ ID NOS: 46

<210> SEQ ID NO 1
<211> LENGTH: 2
<212> TYPE: PRT
<213> ORGANISM: Artificial sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: Palmitic acid coupled to the N-terminus
<220> FEATURE:
<221> NAME/KEY: MISC_FEATURE
<222> LOCATION: (2)..(2)
<223> OTHER INFORMATION: D-Lys
<220> FEATURE:
<221> NAME/KEY: MOD_RES
<222> LOCATION: (2)..(2)
<223> OTHER INFORMATION: AMIDATION

<400> SEQUENCE: 1

Lys Lys
1

<210> SEQ ID NO 2
<211> LENGTH: 3
<212> TYPE: PRT
<213> ORGANISM: Artificial sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: Palmitic acid coupled to the N-terminus
<220> FEATURE:
<221> NAME/KEY: MOD_RES
<222> LOCATION: (3)..(3)
<223> OTHER INFORMATION: Amidation

<400> SEQUENCE: 2

Lys Lys Lys
1

<210> SEQ ID NO 3
<211> LENGTH: 3
<212> TYPE: PRT
<213> ORGANISM: Artificial sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: Palmitic acid coupled to the N-terminus
<220> FEATURE:
<221> NAME/KEY: MISC_FEATURE
<222> LOCATION: (2)..(2)
<223> OTHER INFORMATION: D-Lys
<220> FEATURE:
<221> NAME/KEY: MOD_RES
```

```
<222> LOCATION: (3)..(3)
<223> OTHER INFORMATION: AMIDATION

<400> SEQUENCE: 3

Lys Lys Lys
1

<210> SEQ ID NO 4
<211> LENGTH: 4
<212> TYPE: PRT
<213> ORGANISM: Artificial sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: Palmitic acid coupled to the N-terminus
<220> FEATURE:
<221> NAME/KEY: MISC_FEATURE
<222> LOCATION: (4)..(4)
<223> OTHER INFORMATION: D-Lys
<220> FEATURE:
<221> NAME/KEY: MOD_RES
<222> LOCATION: (4)..(4)
<223> OTHER INFORMATION: AMIDATION

<400> SEQUENCE: 4

Lys Gly Gly Lys
1

<210> SEQ ID NO 5
<211> LENGTH: 4
<212> TYPE: PRT
<213> ORGANISM: Artificial sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: Palmitic acid coupled to the N-terminus
<220> FEATURE:
<221> NAME/KEY: MISC_FEATURE
<222> LOCATION: (3)..(3)
<223> OTHER INFORMATION: D-Leu
<220> FEATURE:
<221> NAME/KEY: MOD_RES
<222> LOCATION: (4)..(4)
<223> OTHER INFORMATION: AMIDATION

<400> SEQUENCE: 5

Lys Leu Leu Lys
1

<210> SEQ ID NO 6
<211> LENGTH: 4
<212> TYPE: PRT
<213> ORGANISM: Artificial sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: Palmitic acid coupled to the N-terminus
<220> FEATURE:
<221> NAME/KEY: MISC_FEATURE
<222> LOCATION: (3)..(3)
<223> OTHER INFORMATION: D-Ala
<220> FEATURE:
<221> NAME/KEY: MOD_RES
<222> LOCATION: (4)..(4)
<223> OTHER INFORMATION: AMIDATION

<400> SEQUENCE: 6
```

-continued

```
Lys Ala Ala Lys
1

<210> SEQ ID NO 7
<211> LENGTH: 6
<212> TYPE: PRT
<213> ORGANISM: Artificial sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: Palmitic acid coupled to the N-terminus
<220> FEATURE:
<221> NAME/KEY: MISC_FEATURE
<222> LOCATION: (2)..(2)
<223> OTHER INFORMATION: D-Leu
<220> FEATURE:
<221> NAME/KEY: MISC_FEATURE
<222> LOCATION: (3)..(3)
<223> OTHER INFORMATION: D-Leu
<220> FEATURE:
<221> NAME/KEY: MOD_RES
<222> LOCATION: (6)..(6)
<223> OTHER INFORMATION: AMIDATION

<400> SEQUENCE: 7

Lys Leu Leu Leu Lys Leu
1               5

<210> SEQ ID NO 8
<211> LENGTH: 6
<212> TYPE: PRT
<213> ORGANISM: Artificial sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: Palmitic acid coupled to the N-terminus
<220> FEATURE:
<221> NAME/KEY: MISC_FEATURE
<222> LOCATION: (2)..(2)
<223> OTHER INFORMATION: D-Ile
<220> FEATURE:
<221> NAME/KEY: MISC_FEATURE
<222> LOCATION: (3)..(3)
<223> OTHER INFORMATION: D-Ile
<220> FEATURE:
<221> NAME/KEY: MOD_RES
<222> LOCATION: (6)..(6)
<223> OTHER INFORMATION: AMIDATION

<400> SEQUENCE: 8

Lys Ile Ile Ile Lys Ile
1               5

<210> SEQ ID NO 9
<211> LENGTH: 6
<212> TYPE: PRT
<213> ORGANISM: Artificial sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: Palmitic acid coupled to the N-terminus
<220> FEATURE:
<221> NAME/KEY: MISC_FEATURE
<222> LOCATION: (2)..(2)
<223> OTHER INFORMATION: D-Val
<220> FEATURE:
<221> NAME/KEY: MISC_FEATURE
```

```
<222> LOCATION: (3)..(3)
<223> OTHER INFORMATION: D-Val
<220> FEATURE:
<221> NAME/KEY: MOD_RES
<222> LOCATION: (6)..(6)
<223> OTHER INFORMATION: AMIDATION

<400> SEQUENCE: 9

Lys Val Val Val Lys Val
1               5

<210> SEQ ID NO 10
<211> LENGTH: 6
<212> TYPE: PRT
<213> ORGANISM: Artificial sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: Palmitic acid coupled to the N-terminus
<220> FEATURE:
<221> NAME/KEY: MISC_FEATURE
<222> LOCATION: (2)..(2)
<223> OTHER INFORMATION: D-Ala
<220> FEATURE:
<221> NAME/KEY: MISC_FEATURE
<222> LOCATION: (3)..(3)
<223> OTHER INFORMATION: D-Ala
<220> FEATURE:
<221> NAME/KEY: MOD_RES
<222> LOCATION: (6)..(6)
<223> OTHER INFORMATION: AMIDATION

<400> SEQUENCE: 10

Lys Ala Ala Ala Lys Ala
1               5

<210> SEQ ID NO 11
<211> LENGTH: 6
<212> TYPE: PRT
<213> ORGANISM: Artificial sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: Palmitic acid coupled to the N-terminus
<220> FEATURE:
<221> NAME/KEY: MISC_FEATURE
<222> LOCATION: (1)..(1)
<223> OTHER INFORMATION: D-Lys
<220> FEATURE:
<221> NAME/KEY: MISC_FEATURE
<222> LOCATION: (5)..(5)
<223> OTHER INFORMATION: D-Lys
<220> FEATURE:
<221> NAME/KEY: MOD_RES
<222> LOCATION: (6)..(6)
<223> OTHER INFORMATION: AMIDATION

<400> SEQUENCE: 11

Lys Gly Gly Gly Lys Gly
1               5

<210> SEQ ID NO 12
<211> LENGTH: 9
<212> TYPE: PRT
<213> ORGANISM: Artificial sequence
<220> FEATURE:
<223> OTHER INFORMATION: Synthetic peptide
<220> FEATURE:
<221> NAME/KEY: MOD_RES
```

```
<222> LOCATION: (1)..(1)
<223> OTHER INFORMATION: Palmitic acid coupled to the N-terminus
<220> FEATURE:
<221> NAME/KEY: MISC_FEATURE
<222> LOCATION: (3)..(3)
<223> OTHER INFORMATION: D-Leu
<220> FEATURE:
<221> NAME/KEY: MISC_FEATURE
<222> LOCATION: (7)..(7)
<223> OTHER INFORMATION: D-Lys
<220> FEATURE:
<221> NAME/KEY: MISC_FEATURE
<222> LOCATION: (8)..(8)
<223> OTHER INFORMATION: D-Lys
<220> FEATURE:
<221> NAME/KEY: MOD_RES
<222> LOCATION: (9)..(9)
<223> OTHER INFORMATION: AMIDATION

<400> SEQUENCE: 12

Lys Leu Leu Lys Leu Leu Lys Lys Leu
1               5

<210> SEQ ID NO 13
<211> LENGTH: 11
<212> TYPE: PRT
<213> ORGANISM: Artificial sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: Palmitic acid coupled to the N-terminus
<220> FEATURE:
<221> NAME/KEY: MISC_FEATURE
<222> LOCATION: (3)..(3)
<223> OTHER INFORMATION: D-Leu
<220> FEATURE:
<221> NAME/KEY: MISC_FEATURE
<222> LOCATION: (6)..(6)
<223> OTHER INFORMATION: D-Lys
<220> FEATURE:
<221> NAME/KEY: MISC_FEATURE
<222> LOCATION: (8)..(8)
<223> OTHER INFORMATION: D-Leu
<220> FEATURE:
<221> NAME/KEY: MISC_FEATURE
<222> LOCATION: (9)..(9)
<223> OTHER INFORMATION: D-Lys
<220> FEATURE:
<221> NAME/KEY: MOD_RES
<222> LOCATION: (11)..(11)
<223> OTHER INFORMATION: AMIDATION

<400> SEQUENCE: 13

Leu Lys Leu Leu Lys Lys Leu Leu Lys Lys Leu
1               5                   10

<210> SEQ ID NO 14
<211> LENGTH: 12
<212> TYPE: PRT
<213> ORGANISM: Artificial sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: Myristic acid coupled to the N-terminus
<220> FEATURE:
<221> NAME/KEY: MISC_FEATURE
<222> LOCATION: (1)..(1)
<223> OTHER INFORMATION: D-Lys
<220> FEATURE:
<221> NAME/KEY: MISC_FEATURE
<222> LOCATION: (5)..(5)
```

```
<223> OTHER INFORMATION: D-Lys
<220> FEATURE:
<221> NAME/KEY: MISC_FEATURE
<222> LOCATION: (9)..(9)
<223> OTHER INFORMATION: D-Lys
<220> FEATURE:
<221> NAME/KEY: MISC_FEATURE
<222> LOCATION: (12)..(12)
<223> OTHER INFORMATION: D-Lys
<220> FEATURE:
<221> NAME/KEY: MOD_RES
<222> LOCATION: (12)..(12)
<223> OTHER INFORMATION: AMIDATION

<400> SEQUENCE: 14

Lys Gly Gly Gly Lys Gly Gly Gly Lys Gly Gly Lys
1               5                   10

<210> SEQ ID NO 15
<211> LENGTH: 12
<212> TYPE: PRT
<213> ORGANISM: Artificial sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: Palmitic acid coupled to the N-terminus
<220> FEATURE:
<221> NAME/KEY: MISC_FEATURE
<222> LOCATION: (1)..(1)
<223> OTHER INFORMATION: D-Lys
<220> FEATURE:
<221> NAME/KEY: MISC_FEATURE
<222> LOCATION: (5)..(5)
<223> OTHER INFORMATION: D-Lys
<220> FEATURE:
<221> NAME/KEY: MISC_FEATURE
<222> LOCATION: (9)..(9)
<223> OTHER INFORMATION: D-Lys
<220> FEATURE:
<221> NAME/KEY: MISC_FEATURE
<222> LOCATION: (12)..(12)
<223> OTHER INFORMATION: D-Lys
<220> FEATURE:
<221> NAME/KEY: MOD_RES
<222> LOCATION: (12)..(12)
<223> OTHER INFORMATION: AMIDATION

<400> SEQUENCE: 15

Lys Gly Gly Gly Lys Gly Gly Gly Lys Gly Gly Lys
1               5                   10

<210> SEQ ID NO 16
<211> LENGTH: 12
<212> TYPE: PRT
<213> ORGANISM: Artificial sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: Palmitic acid coupled to the N-terminus
<220> FEATURE:
<221> NAME/KEY: MISC_FEATURE
<222> LOCATION: (3)..(3)
<223> OTHER INFORMATION: D-Ala
<220> FEATURE:
<221> NAME/KEY: MISC_FEATURE
<222> LOCATION: (4)..(4)
<223> OTHER INFORMATION: D-Ala
<220> FEATURE:
<221> NAME/KEY: MISC_FEATURE
<222> LOCATION: (8)..(8)
<223> OTHER INFORMATION: D-Ala
```

```
<220> FEATURE:
<221> NAME/KEY: MISC_FEATURE
<222> LOCATION: (10)..(10)
<223> OTHER INFORMATION: D-Ala
<220> FEATURE:
<221> NAME/KEY: MOD_RES
<222> LOCATION: (12)..(12)
<223> OTHER INFORMATION: AMIDATION

<400> SEQUENCE: 16

Lys Ala Ala Ala Lys Ala Ala Ala Lys Ala Ala Lys
1               5                   10

<210> SEQ ID NO 17
<211> LENGTH: 12
<212> TYPE: PRT
<213> ORGANISM: Artificial sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: Palmitic acid coupled to the N-terminus
<220> FEATURE:
<221> NAME/KEY: MISC_FEATURE
<222> LOCATION: (3)..(3)
<223> OTHER INFORMATION: D-Val
<220> FEATURE:
<221> NAME/KEY: MISC_FEATURE
<222> LOCATION: (4)..(4)
<223> OTHER INFORMATION: D-Val
<220> FEATURE:
<221> NAME/KEY: MISC_FEATURE
<222> LOCATION: (8)..(8)
<223> OTHER INFORMATION: D-Val
<220> FEATURE:
<221> NAME/KEY: MISC_FEATURE
<222> LOCATION: (10)..(10)
<223> OTHER INFORMATION: D-Val
<220> FEATURE:
<221> NAME/KEY: MOD_RES
<222> LOCATION: (12)..(12)
<223> OTHER INFORMATION: AMIDATION

<400> SEQUENCE: 17

Lys Val Val Val Lys Val Val Val Lys Val Val Lys
1               5                   10

<210> SEQ ID NO 18
<211> LENGTH: 12
<212> TYPE: PRT
<213> ORGANISM: Artificial sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: Palmitic acid coupled to the N-terminus
<220> FEATURE:
<221> NAME/KEY: MISC_FEATURE
<222> LOCATION: (3)..(3)
<223> OTHER INFORMATION: D-Ile
<220> FEATURE:
<221> NAME/KEY: MISC_FEATURE
<222> LOCATION: (4)..(4)
<223> OTHER INFORMATION: D-Ile
<220> FEATURE:
<221> NAME/KEY: MISC_FEATURE
<222> LOCATION: (8)..(8)
<223> OTHER INFORMATION: D-Ile
<220> FEATURE:
<221> NAME/KEY: MISC_FEATURE
<222> LOCATION: (10)..(10)
<223> OTHER INFORMATION: D-Ile
<220> FEATURE:
```

```
<221> NAME/KEY: MOD_RES
<222> LOCATION: (12)..(12)
<223> OTHER INFORMATION: AMIDATION

<400> SEQUENCE: 18

Lys Ile Ile Ile Lys Ile Ile Ile Lys Ile Ile Lys
1               5                   10

<210> SEQ ID NO 19
<211> LENGTH: 12
<212> TYPE: PRT
<213> ORGANISM: Artificial sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: Undecanoic acid coupled to the N-terminus
<220> FEATURE:
<221> NAME/KEY: MISC_FEATURE
<222> LOCATION: (3)..(3)
<223> OTHER INFORMATION: D-Leu
<220> FEATURE:
<221> NAME/KEY: MISC_FEATURE
<222> LOCATION: (4)..(4)
<223> OTHER INFORMATION: D-Leu
<220> FEATURE:
<221> NAME/KEY: MISC_FEATURE
<222> LOCATION: (8)..(8)
<223> OTHER INFORMATION: D-Leu
<220> FEATURE:
<221> NAME/KEY: MISC_FEATURE
<222> LOCATION: (10)..(10)
<223> OTHER INFORMATION: D-Leu
<220> FEATURE:
<221> NAME/KEY: MOD_RES
<222> LOCATION: (12)..(12)
<223> OTHER INFORMATION: AMIDATION

<400> SEQUENCE: 19

Lys Leu Leu Leu Lys Leu Leu Leu Lys Leu Leu Lys
1               5                   10

<210> SEQ ID NO 20
<211> LENGTH: 12
<212> TYPE: PRT
<213> ORGANISM: Artificial sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: Palmitic acid coupled to the N-terminus
<220> FEATURE:
<221> NAME/KEY: MISC_FEATURE
<222> LOCATION: (3)..(3)
<223> OTHER INFORMATION: D-Leu
<220> FEATURE:
<221> NAME/KEY: MISC_FEATURE
<222> LOCATION: (4)..(4)
<223> OTHER INFORMATION: D-Leu
<220> FEATURE:
<221> NAME/KEY: MISC_FEATURE
<222> LOCATION: (8)..(8)
<223> OTHER INFORMATION: D-Leu
<220> FEATURE:
<221> NAME/KEY: MISC_FEATURE
<222> LOCATION: (10)..(10)
<223> OTHER INFORMATION: D-Leu
<220> FEATURE:
<221> NAME/KEY: MOD_RES
<222> LOCATION: (12)..(12)
<223> OTHER INFORMATION: AMIDATION

<400> SEQUENCE: 20
```

Lys Leu Leu Leu Lys Leu Leu Leu Lys Leu Leu Lys
1               5                   10

<210> SEQ ID NO 21
<211> LENGTH: 12
<212> TYPE: PRT
<213> ORGANISM: Artificial sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: Decanoic acid coupled to the N-terminus
<220> FEATURE:
<221> NAME/KEY: MISC_FEATURE
<222> LOCATION: (1)..(1)
<223> OTHER INFORMATION: D-Leu
<220> FEATURE:
<221> NAME/KEY: MISC_FEATURE
<222> LOCATION: (4)..(4)
<223> OTHER INFORMATION: D-Leu
<220> FEATURE:
<221> NAME/KEY: MISC_FEATURE
<222> LOCATION: (5)..(5)
<223> OTHER INFORMATION: D-Leu
<220> FEATURE:
<221> NAME/KEY: MISC_FEATURE
<222> LOCATION: (8)..(8)
<223> OTHER INFORMATION: D-Leu
<220> FEATURE:
<221> NAME/KEY: MISC_FEATURE
<222> LOCATION: (9)..(9)
<223> OTHER INFORMATION: D-Leu
<220> FEATURE:
<221> NAME/KEY: MISC_FEATURE
<222> LOCATION: (12)..(12)
<223> OTHER INFORMATION: D-Leu
<220> FEATURE:
<221> NAME/KEY: MOD_RES
<222> LOCATION: (12)..(12)
<223> OTHER INFORMATION: AMIDATION

<400> SEQUENCE: 21

Leu Lys Lys Leu Leu Lys Lys Leu Leu Lys Lys Leu
1               5                   10

<210> SEQ ID NO 22
<211> LENGTH: 12
<212> TYPE: PRT
<213> ORGANISM: Artificial sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: Dodecanoic acid coupled to the N-terminus
<220> FEATURE:
<221> NAME/KEY: MISC_FEATURE
<222> LOCATION: (1)..(1)
<223> OTHER INFORMATION: D-Leu
<220> FEATURE:
<221> NAME/KEY: MISC_FEATURE
<222> LOCATION: (4)..(4)
<223> OTHER INFORMATION: D-Leu
<220> FEATURE:
<221> NAME/KEY: MISC_FEATURE
<222> LOCATION: (5)..(5)
<223> OTHER INFORMATION: D-Leu
<220> FEATURE:
<221> NAME/KEY: MISC_FEATURE
<222> LOCATION: (8)..(8)
<223> OTHER INFORMATION: D-Leu
<220> FEATURE:
<221> NAME/KEY: MISC_FEATURE
<222> LOCATION: (9)..(9)

-continued

```
<223> OTHER INFORMATION: D-Leu
<220> FEATURE:
<221> NAME/KEY: MISC_FEATURE
<222> LOCATION: (12)..(12)
<223> OTHER INFORMATION: D-Leu
<220> FEATURE:
<221> NAME/KEY: MOD_RES
<222> LOCATION: (12)..(12)
<223> OTHER INFORMATION: AMIDATION

<400> SEQUENCE: 22

Leu Lys Lys Leu Leu Lys Lys Leu Leu Lys Lys Leu
1               5                   10

<210> SEQ ID NO 23
<211> LENGTH: 12
<212> TYPE: PRT
<213> ORGANISM: Artificial sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: Myristic acid coupled to the N-terminus
<220> FEATURE:
<221> NAME/KEY: MISC_FEATURE
<222> LOCATION: (1)..(1)
<223> OTHER INFORMATION: D-Leu
<220> FEATURE:
<221> NAME/KEY: MISC_FEATURE
<222> LOCATION: (4)..(4)
<223> OTHER INFORMATION: D-Leu
<220> FEATURE:
<221> NAME/KEY: MISC_FEATURE
<222> LOCATION: (5)..(5)
<223> OTHER INFORMATION: D-Leu
<220> FEATURE:
<221> NAME/KEY: MISC_FEATURE
<222> LOCATION: (8)..(8)
<223> OTHER INFORMATION: D-Leu
<220> FEATURE:
<221> NAME/KEY: MISC_FEATURE
<222> LOCATION: (9)..(9)
<223> OTHER INFORMATION: D-Leu
<220> FEATURE:
<221> NAME/KEY: MISC_FEATURE
<222> LOCATION: (12)..(12)
<223> OTHER INFORMATION: D-Leu
<220> FEATURE:
<221> NAME/KEY: MOD_RES
<222> LOCATION: (12)..(12)
<223> OTHER INFORMATION: AMIDATION

<400> SEQUENCE: 23

Leu Lys Lys Leu Leu Lys Lys Leu Leu Lys Lys Leu
1               5                   10

<210> SEQ ID NO 24
<211> LENGTH: 12
<212> TYPE: PRT
<213> ORGANISM: Artificial sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: Palmitic acid coupled to the N-terminus
<220> FEATURE:
<221> NAME/KEY: MISC_FEATURE
<222> LOCATION: (1)..(1)
<223> OTHER INFORMATION: D-Leu
<220> FEATURE:
<221> NAME/KEY: MISC_FEATURE
<222> LOCATION: (4)..(4)
<223> OTHER INFORMATION: D-Leu
```

```
<220> FEATURE:
<221> NAME/KEY: MISC_FEATURE
<222> LOCATION: (5)..(5)
<223> OTHER INFORMATION: D-Leu
<220> FEATURE:
<221> NAME/KEY: MISC_FEATURE
<222> LOCATION: (8)..(8)
<223> OTHER INFORMATION: D-Leu
<220> FEATURE:
<221> NAME/KEY: MISC_FEATURE
<222> LOCATION: (9)..(9)
<223> OTHER INFORMATION: D-Leu
<220> FEATURE:
<221> NAME/KEY: MISC_FEATURE
<222> LOCATION: (12)..(12)
<223> OTHER INFORMATION: D-Leu
<220> FEATURE:
<221> NAME/KEY: MOD_RES
<222> LOCATION: (12)..(12)
<223> OTHER INFORMATION: AMIDATION

<400> SEQUENCE: 24

Leu Lys Lys Leu Leu Lys Lys Leu Leu Lys Lys Leu
1               5                   10

<210> SEQ ID NO 25
<211> LENGTH: 4
<212> TYPE: PRT
<213> ORGANISM: Artificial sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: Palmitic acid coupled to the N-terminus
<220> FEATURE:
<221> NAME/KEY: MISC_FEATURE
<222> LOCATION: (3)..(3)
<223> OTHER INFORMATION: D-Leu
<220> FEATURE:
<221> NAME/KEY: MOD_RES
<222> LOCATION: (4)..(4)
<223> OTHER INFORMATION: AMIDATION

<400> SEQUENCE: 25

Arg Leu Leu Arg
1

<210> SEQ ID NO 26
<211> LENGTH: 12
<212> TYPE: PRT
<213> ORGANISM: Artificial sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: Dodecanoic acid coupled to the N-terminus
<220> FEATURE:
<221> NAME/KEY: MISC_FEATURE
<222> LOCATION: (1)..(1)
<223> OTHER INFORMATION: D-Leu
<220> FEATURE:
<221> NAME/KEY: MISC_FEATURE
<222> LOCATION: (4)..(4)
<223> OTHER INFORMATION: D-Leu
<220> FEATURE:
<221> NAME/KEY: MISC_FEATURE
<222> LOCATION: (5)..(5)
<223> OTHER INFORMATION: D-Leu
<220> FEATURE:
<221> NAME/KEY: MISC_FEATURE
<222> LOCATION: (8)..(8)
<223> OTHER INFORMATION: D-Leu
<220> FEATURE:
```

```
<221> NAME/KEY: MISC_FEATURE
<222> LOCATION: (9)..(9)
<223> OTHER INFORMATION: D-Leu
<220> FEATURE:
<221> NAME/KEY: MISC_FEATURE
<222> LOCATION: (12)..(12)
<223> OTHER INFORMATION: D-Leu
<220> FEATURE:
<221> NAME/KEY: MOD_RES
<222> LOCATION: (12)..(12)
<223> OTHER INFORMATION: AMIDATION

<400> SEQUENCE: 26

Leu Arg Arg Leu Leu Arg Arg Leu Leu Arg Arg Leu
1               5                   10

<210> SEQ ID NO 27
<211> LENGTH: 12
<212> TYPE: PRT
<213> ORGANISM: Artificial sequence
<220> FEATURE:
<223> OTHER INFORMATION: Synthetic peptdie
<220> FEATURE:
<221> NAME/KEY: MOD_RES
<222> LOCATION: (1)..(1)
<223> OTHER INFORMATION: Dodecanoic acid coupled to the N-terminus
<220> FEATURE:
<221> NAME/KEY: MISC_FEATURE
<222> LOCATION: (1)..(1)
<223> OTHER INFORMATION: D-Leu
<220> FEATURE:
<221> NAME/KEY: MISC_FEATURE
<222> LOCATION: (4)..(4)
<223> OTHER INFORMATION: D-Leu
<220> FEATURE:
<221> NAME/KEY: MISC_FEATURE
<222> LOCATION: (5)..(5)
<223> OTHER INFORMATION: D-Leu
<220> FEATURE:
<221> NAME/KEY: MISC_FEATURE
<222> LOCATION: (8)..(8)
<223> OTHER INFORMATION: D-Leu
<220> FEATURE:
<221> NAME/KEY: MISC_FEATURE
<222> LOCATION: (9)..(9)
<223> OTHER INFORMATION: D-Leu
<220> FEATURE:
<221> NAME/KEY: MISC_FEATURE
<222> LOCATION: (12)..(12)
<223> OTHER INFORMATION: D-Leu
<220> FEATURE:
<221> NAME/KEY: MOD_RES
<222> LOCATION: (12)..(12)
<223> OTHER INFORMATION: AMIDATION

<400> SEQUENCE: 27

Leu His His Leu Leu His His Leu Leu His His Leu
1               5                   10

<210> SEQ ID NO 28
<211> LENGTH: 11
<212> TYPE: PRT
<213> ORGANISM: Artificial sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: Palmitic acid coupled to the N-terminus
<220> FEATURE:
<221> NAME/KEY: MISC_FEATURE
<222> LOCATION: (3)..(3)
<223> OTHER INFORMATION: D-Leu
<220> FEATURE:
<221> NAME/KEY: MISC_FEATURE
```

```
<222> LOCATION: (7)..(7)
<223> OTHER INFORMATION: D-Lys
<220> FEATURE:
<221> NAME/KEY: MISC_FEATURE
<222> LOCATION: (8)..(8)
<223> OTHER INFORMATION: D-Lys
<220> FEATURE:
<221> NAME/KEY: MISC_FEATURE
<222> LOCATION: (10)..(10)
<223> OTHER INFORMATION: D-Leu
<220> FEATURE:
<221> NAME/KEY: MOD_RES
<222> LOCATION: (11)..(11)
<223> OTHER INFORMATION: AMIDATION

<400> SEQUENCE: 28

Lys Leu Leu Arg Leu Leu Lys Lys Leu Leu Arg
1               5                   10

<210> SEQ ID NO 29
<211> LENGTH: 12
<212> TYPE: PRT
<213> ORGANISM: Artificial sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: Palmitic acid coupled to the N-terminus
<220> FEATURE:
<221> NAME/KEY: MISC_FEATURE
<222> LOCATION: (3)..(3)
<223> OTHER INFORMATION: D-Leu
<220> FEATURE:
<221> NAME/KEY: MISC_FEATURE
<222> LOCATION: (6)..(6)
<223> OTHER INFORMATION: D-Leu
<220> FEATURE:
<221> NAME/KEY: MISC_FEATURE
<222> LOCATION: (8)..(8)
<223> OTHER INFORMATION: D-Lys
<220> FEATURE:
<221> NAME/KEY: MISC_FEATURE
<222> LOCATION: (9)..(9)
<223> OTHER INFORMATION: D-Lys
<220> FEATURE:
<221> NAME/KEY: MOD_RES
<222> LOCATION: (12)..(12)
<223> OTHER INFORMATION: AMIDATION

<400> SEQUENCE: 29

Lys Leu Leu Leu Arg Leu Leu Lys Lys Leu Leu Arg
1               5                   10

<210> SEQ ID NO 30
<211> LENGTH: 12
<212> TYPE: PRT
<213> ORGANISM: Artificial sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: Palmitic acid coupled to the N-terminus
<220> FEATURE:
<221> NAME/KEY: MISC_FEATURE
<222> LOCATION: (3)..(3)
<223> OTHER INFORMATION: D-Leu
<220> FEATURE:
<221> NAME/KEY: MISC_FEATURE
<222> LOCATION: (7)..(7)
<223> OTHER INFORMATION: D-Lys
<220> FEATURE:
<221> NAME/KEY: MISC_FEATURE
<222> LOCATION: (8)..(8)
```

```
<223> OTHER INFORMATION: D-Lys
<220> FEATURE:
<221> NAME/KEY: MISC_FEATURE
<222> LOCATION: (10)..(10)
<223> OTHER INFORMATION: D-Leu
<220> FEATURE:
<221> NAME/KEY: MOD_RES
<222> LOCATION: (12)..(12)
<223> OTHER INFORMATION: AMIDATION

<400> SEQUENCE: 30

Lys Leu Leu Arg Leu Leu Lys Lys Leu Leu Arg Leu
1               5                   10

<210> SEQ ID NO 31
<211> LENGTH: 14
<212> TYPE: PRT
<213> ORGANISM: Artificial sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: Palmitic acid coupled to the N-terminus
<220> FEATURE:
<221> NAME/KEY: MISC_FEATURE
<222> LOCATION: (3)..(3)
<223> OTHER INFORMATION: D-Leu
<220> FEATURE:
<221> NAME/KEY: MISC_FEATURE
<222> LOCATION: (6)..(6)
<223> OTHER INFORMATION: D-Leu
<220> FEATURE:
<221> NAME/KEY: MISC_FEATURE
<222> LOCATION: (8)..(8)
<223> OTHER INFORMATION: D-Lys
<220> FEATURE:
<221> NAME/KEY: MISC_FEATURE
<222> LOCATION: (9)..(9)
<223> OTHER INFORMATION: D-Lys
<220> FEATURE:
<221> NAME/KEY: MISC_FEATURE
<222> LOCATION: (13)..(13)
<223> OTHER INFORMATION: D-Leu
<220> FEATURE:
<221> NAME/KEY: MOD_RES
<222> LOCATION: (14)..(14)
<223> OTHER INFORMATION: AMIDATION

<400> SEQUENCE: 31

Lys Leu Leu Leu Arg Leu Leu Lys Lys Leu Leu Arg Leu Lys
1               5                   10

<210> SEQ ID NO 32
<211> LENGTH: 12
<212> TYPE: PRT
<213> ORGANISM: Artificial sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: Dodecanoic acid coupled to the N-terminus
<220> FEATURE:
<221> NAME/KEY: MISC_FEATURE
<222> LOCATION: (1)..(1)
<223> OTHER INFORMATION: D-Leu
<220> FEATURE:
<221> NAME/KEY: MISC_FEATURE
<222> LOCATION: (4)..(4)
<223> OTHER INFORMATION: D-Leu
<220> FEATURE:
<221> NAME/KEY: MISC_FEATURE
<222> LOCATION: (5)..(5)
<223> OTHER INFORMATION: D-Leu
```

```
<220> FEATURE:
<221> NAME/KEY: MISC_FEATURE
<222> LOCATION: (8)..(8)
<223> OTHER INFORMATION: D-Leu
<220> FEATURE:
<221> NAME/KEY: MISC_FEATURE
<222> LOCATION: (9)..(9)
<223> OTHER INFORMATION: D-Leu
<220> FEATURE:
<221> NAME/KEY: MISC_FEATURE
<222> LOCATION: (12)..(12)
<223> OTHER INFORMATION: D-Leu
<220> FEATURE:
<221> NAME/KEY: MOD_RES
<222> LOCATION: (12)..(12)
<223> OTHER INFORMATION: AMIDATION

<400> SEQUENCE: 32

Leu Arg His Leu Leu Arg His Leu Leu Arg His Leu
1               5                   10

<210> SEQ ID NO 33
<211> LENGTH: 12
<212> TYPE: PRT
<213> ORGANISM: Artificial sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: Dodecanoic acid coupled to the N-terminus
<220> FEATURE:
<221> NAME/KEY: MISC_FEATURE
<222> LOCATION: (1)..(1)
<223> OTHER INFORMATION: D-Leu
<220> FEATURE:
<221> NAME/KEY: MISC_FEATURE
<222> LOCATION: (4)..(4)
<223> OTHER INFORMATION: D-Leu
<220> FEATURE:
<221> NAME/KEY: MISC_FEATURE
<222> LOCATION: (5)..(5)
<223> OTHER INFORMATION: D-Leu
<220> FEATURE:
<221> NAME/KEY: MISC_FEATURE
<222> LOCATION: (8)..(8)
<223> OTHER INFORMATION: D-Leu
<220> FEATURE:
<221> NAME/KEY: MISC_FEATURE
<222> LOCATION: (9)..(9)
<223> OTHER INFORMATION: D-Leu
<220> FEATURE:
<221> NAME/KEY: MISC_FEATURE
<222> LOCATION: (12)..(12)
<223> OTHER INFORMATION: D-Leu
<220> FEATURE:
<221> NAME/KEY: MOD_RES
<222> LOCATION: (12)..(12)
<223> OTHER INFORMATION: AMIDATION

<400> SEQUENCE: 33

Leu Lys His Leu Leu Lys His Leu Leu Lys His Leu
1               5                   10

<210> SEQ ID NO 34
<211> LENGTH: 7
<212> TYPE: PRT
<213> ORGANISM: Artificial sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: Palmitic acid coupled to the N-terminus
<220> FEATURE:
```

```
<221> NAME/KEY: MISC_FEATURE
<222> LOCATION: (2)..(2)
<223> OTHER INFORMATION: D-Leu
<220> FEATURE:
<221> NAME/KEY: MISC_FEATURE
<222> LOCATION: (5)..(5)
<223> OTHER INFORMATION: D-Leu
<220> FEATURE:
<221> NAME/KEY: MOD_RES
<222> LOCATION: (7)..(7)
<223> OTHER INFORMATION: AMIDATION

<400> SEQUENCE: 34

Leu Leu Leu Arg Leu Gly Leu
1               5

<210> SEQ ID NO 35
<211> LENGTH: 7
<212> TYPE: PRT
<213> ORGANISM: Artificial sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: Palmitic acid coupled to the N-terminus
<220> FEATURE:
<221> NAME/KEY: MISC_FEATURE
<222> LOCATION: (2)..(2)
<223> OTHER INFORMATION: D-Leu
<220> FEATURE:
<221> NAME/KEY: MISC_FEATURE
<222> LOCATION: (6)..(6)
<223> OTHER INFORMATION: D-Lys
<220> FEATURE:
<221> NAME/KEY: MOD_RES
<222> LOCATION: (7)..(7)
<223> OTHER INFORMATION: AMIDATION

<400> SEQUENCE: 35

Leu Leu Lys Leu Leu Lys Gly
1               5

<210> SEQ ID NO 36
<211> LENGTH: 4
<212> TYPE: PRT
<213> ORGANISM: Artificial sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: Palmitic acid coupled to the N-terminus
<220> FEATURE:
<221> NAME/KEY: MISC_FEATURE
<222> LOCATION: (3)..(3)
<223> OTHER INFORMATION: D-Lys
<220> FEATURE:
<221> NAME/KEY: MOD_RES
<222> LOCATION: (4)..(4)
<223> OTHER INFORMATION: AMIDATION

<400> SEQUENCE: 36

Glu Lys Lys Lys
1

<210> SEQ ID NO 37
<211> LENGTH: 4
<212> TYPE: PRT
<213> ORGANISM: Artificial sequence
<220> FEATURE:
<223> OTHER INFORMATION: Synthetic peptide
<220> FEATURE:
```

```
<221> NAME/KEY: MOD_RES
<222> LOCATION: (1)..(1)
<223> OTHER INFORMATION: Palmitic acid coupled to the N-terminus
<220> FEATURE:
<221> NAME/KEY: MISC_FEATURE
<222> LOCATION: (2)..(2)
<223> OTHER INFORMATION: D-Lys
<220> FEATURE:
<221> NAME/KEY: MOD_RES
<222> LOCATION: (4)..(4)
<223> OTHER INFORMATION: AMIDATION

<400> SEQUENCE: 37

Lys Lys Glu Lys
1

<210> SEQ ID NO 38
<211> LENGTH: 3
<212> TYPE: PRT
<213> ORGANISM: Artificial sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: Palmitic acid coupled to the N-terminus
<220> FEATURE:
<221> NAME/KEY: MISC_FEATURE
<222> LOCATION: (2)..(2)
<223> OTHER INFORMATION: D-Lys
<220> FEATURE:
<221> NAME/KEY: MOD_RES
<222> LOCATION: (3)..(3)
<223> OTHER INFORMATION: AMIDATION

<400> SEQUENCE: 38

Glu Lys Lys
1

<210> SEQ ID NO 39
<211> LENGTH: 8
<212> TYPE: PRT
<213> ORGANISM: Artificial sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: Palmitic acid coupled to the N-terminus
<220> FEATURE:
<221> NAME/KEY: MISC_FEATURE
<222> LOCATION: (1)..(8)
<223> OTHER INFORMATION: Disulfide bond
<220> FEATURE:
<221> NAME/KEY: MISC_FEATURE
<222> LOCATION: (3)..(3)
<223> OTHER INFORMATION: D-Leu
<220> FEATURE:
<221> NAME/KEY: MISC_FEATURE
<222> LOCATION: (4)..(4)
<223> OTHER INFORMATION: D-Leu
<220> FEATURE:
<221> NAME/KEY: MOD_RES
<222> LOCATION: (8)..(8)
<223> OTHER INFORMATION: AMIDATION

<400> SEQUENCE: 39

Cys Lys Leu Leu Leu Lys Leu Cys
1               5

<210> SEQ ID NO 40
<211> LENGTH: 8
<212> TYPE: PRT
```

```
<213> ORGANISM: Artificial sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: Palmitic acid coupled to the N-terminus
<220> FEATURE:
<221> NAME/KEY: MISC_FEATURE
<222> LOCATION: (1)..(8)
<223> OTHER INFORMATION: Disulfide bond
<220> FEATURE:
<221> NAME/KEY: MISC_FEATURE
<222> LOCATION: (3)..(3)
<223> OTHER INFORMATION: D-Ala
<220> FEATURE:
<221> NAME/KEY: MISC_FEATURE
<222> LOCATION: (4)..(4)
<223> OTHER INFORMATION: D-Ala
<220> FEATURE:
<221> NAME/KEY: MOD_RES
<222> LOCATION: (8)..(8)
<223> OTHER INFORMATION: AMIDATION

<400> SEQUENCE: 40

Cys Lys Ala Ala Ala Lys Ala Cys
1               5

<210> SEQ ID NO 41
<211> LENGTH: 8
<212> TYPE: PRT
<213> ORGANISM: Artificial sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: Palmitic acid coupled to the N-terminus
<220> FEATURE:
<221> NAME/KEY: MISC_FEATURE
<222> LOCATION: (1)..(8)
<223> OTHER INFORMATION: Disulfide bond
<220> FEATURE:
<221> NAME/KEY: MISC_FEATURE
<222> LOCATION: (2)..(2)
<223> OTHER INFORMATION: D-Lys
<220> FEATURE:
<221> NAME/KEY: MISC_FEATURE
<222> LOCATION: (6)..(6)
<223> OTHER INFORMATION: D-Lys
<220> FEATURE:
<221> NAME/KEY: MOD_RES
<222> LOCATION: (8)..(8)
<223> OTHER INFORMATION: AMIDATION

<400> SEQUENCE: 41

Cys Lys Gly Gly Gly Lys Gly Cys
1               5

<210> SEQ ID NO 42
<211> LENGTH: 14
<212> TYPE: PRT
<213> ORGANISM: Artificial sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: Palmitic acid coupled to the N-terminus
<220> FEATURE:
<221> NAME/KEY: MISC_FEATURE
<222> LOCATION: (1)..(14)
<223> OTHER INFORMATION: Disulfide bond
<220> FEATURE:
<221> NAME/KEY: MISC_FEATURE
```

```
<222> LOCATION: (3)..(3)
<223> OTHER INFORMATION: D-Ile
<220> FEATURE:
<221> NAME/KEY: MISC_FEATURE
<222> LOCATION: (4)..(4)
<223> OTHER INFORMATION: D-Ile
<220> FEATURE:
<221> NAME/KEY: MISC_FEATURE
<222> LOCATION: (9)..(9)
<223> OTHER INFORMATION: D-Ile
<220> FEATURE:
<221> NAME/KEY: MISC_FEATURE
<222> LOCATION: (11)..(11)
<223> OTHER INFORMATION: D-Ile
<220> FEATURE:
<221> NAME/KEY: MOD_RES
<222> LOCATION: (14)..(14)
<223> OTHER INFORMATION: AMIDATION

<400> SEQUENCE: 42

Cys Lys Ile Ile Ile Lys Ile Ile Ile Lys Ile Ile Lys Cys
1               5                   10

<210> SEQ ID NO 43
<211> LENGTH: 14
<212> TYPE: PRT
<213> ORGANISM: Artificial sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: Palmitic acid coupled to the N-terminus
<220> FEATURE:
<221> NAME/KEY: MISC_FEATURE
<222> LOCATION: (1)..(14)
<223> OTHER INFORMATION: Disulfide bond
<220> FEATURE:
<221> NAME/KEY: MISC_FEATURE
<222> LOCATION: (4)..(4)
<223> OTHER INFORMATION: D-Ala
<220> FEATURE:
<221> NAME/KEY: MISC_FEATURE
<222> LOCATION: (5)..(5)
<223> OTHER INFORMATION: D-Ala
<220> FEATURE:
<221> NAME/KEY: MISC_FEATURE
<222> LOCATION: (9)..(9)
<223> OTHER INFORMATION: D-Ala
<220> FEATURE:
<221> NAME/KEY: MISC_FEATURE
<222> LOCATION: (11)..(11)
<223> OTHER INFORMATION: D-Ala
<220> FEATURE:
<221> NAME/KEY: MOD_RES
<222> LOCATION: (14)..(14)
<223> OTHER INFORMATION: AMIDATION

<400> SEQUENCE: 43

Cys Lys Ala Ala Ala Lys Ala Ala Ala Lys Ala Ala Lys Cys
1               5                   10

<210> SEQ ID NO 44
<211> LENGTH: 14
<212> TYPE: PRT
<213> ORGANISM: Artificial sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: Myristic acid coupled to the N-terminus
<220> FEATURE:
<221> NAME/KEY: MISC_FEATURE
<222> LOCATION: (1)..(14)
```

```
<223> OTHER INFORMATION: Disulfide bond
<220> FEATURE:
<221> NAME/KEY: MISC_FEATURE
<222> LOCATION: (4)..(4)
<223> OTHER INFORMATION: D-Ala
<220> FEATURE:
<221> NAME/KEY: MISC_FEATURE
<222> LOCATION: (5)..(5)
<223> OTHER INFORMATION: D-Ala
<220> FEATURE:
<221> NAME/KEY: MISC_FEATURE
<222> LOCATION: (9)..(9)
<223> OTHER INFORMATION: D-Ala
<220> FEATURE:
<221> NAME/KEY: MISC_FEATURE
<222> LOCATION: (11)..(11)
<223> OTHER INFORMATION: D-Ala
<220> FEATURE:
<221> NAME/KEY: MOD_RES
<222> LOCATION: (14)..(14)
<223> OTHER INFORMATION: AMIDATION

<400> SEQUENCE: 44

Cys Lys Ala Ala Ala Lys Ala Ala Ala Lys Ala Ala Lys Cys
1               5                   10

<210> SEQ ID NO 45
<211> LENGTH: 14
<212> TYPE: PRT
<213> ORGANISM: Artificial sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: Myristic acid coupled to the N-terminus
<220> FEATURE:
<221> NAME/KEY: MISC_FEATURE
<222> LOCATION: (1)..(14)
<223> OTHER INFORMATION: Disulfide bond
<220> FEATURE:
<221> NAME/KEY: MISC_FEATURE
<222> LOCATION: (2)..(2)
<223> OTHER INFORMATION: D-Lys
<220> FEATURE:
<221> NAME/KEY: MISC_FEATURE
<222> LOCATION: (6)..(6)
<223> OTHER INFORMATION: D-Lys
<220> FEATURE:
<221> NAME/KEY: MISC_FEATURE
<222> LOCATION: (10)..(10)
<223> OTHER INFORMATION: D-Lys
<220> FEATURE:
<221> NAME/KEY: MISC_FEATURE
<222> LOCATION: (13)..(13)
<223> OTHER INFORMATION: D-Lys
<220> FEATURE:
<221> NAME/KEY: MOD_RES
<222> LOCATION: (14)..(14)
<223> OTHER INFORMATION: AMIDATION

<400> SEQUENCE: 45

Cys Lys Gly Gly Gly Lys Gly Gly Gly Lys Gly Gly Lys Cys
1               5                   10

<210> SEQ ID NO 46
<211> LENGTH: 14
<212> TYPE: PRT
<213> ORGANISM: Artificial sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: Palmitic acid coupled to the N-terminus
```

```
<220> FEATURE:
<221> NAME/KEY: MISC_FEATURE
<222> LOCATION: (1)..(14)
<223> OTHER INFORMATION: Disulfide bond
<220> FEATURE:
<221> NAME/KEY: MISC_FEATURE
<222> LOCATION: (2)..(2)
<223> OTHER INFORMATION: D-Lys
<220> FEATURE:
<221> NAME/KEY: MISC_FEATURE
<222> LOCATION: (6)..(6)
<223> OTHER INFORMATION: D-Lys
<220> FEATURE:
<221> NAME/KEY: MISC_FEATURE
<222> LOCATION: (10)..(10)
<223> OTHER INFORMATION: D-Lys
<220> FEATURE:
<221> NAME/KEY: MISC_FEATURE
<222> LOCATION: (13)..(13)
<223> OTHER INFORMATION: D-Lys
<220> FEATURE:
<221> NAME/KEY: MOD_RES
<222> LOCATION: (14)..(14)
<223> OTHER INFORMATION: AMIDATION

<400> SEQUENCE: 46

Cys Lys Gly Gly Gly Lys Gly Gly Gly Lys Gly Gly Lys Cys
1               5                   10
```

US 7,671,011 B2

ANTIMICROBIAL AND ANTICANCER LIPOPEPTIDES

CROSS REFERENCE TO RELATED APPLICATIONS

This application is a 371 filing of International Application PCT/IL2004/000544 filed on Jun. 18, 2004 and published in English as International Publication No. WO 2004/110341 A2 on Dec. 23, 2004, and claims priority from U.S. application No. 60/479,465 filed Jun. 19, 2003, which applications are hereby incorporated by reference herein in their entirety.

FIELD OF THE INVENTION

The present invention relates to lipophilic conjugates comprising fatty acids couples to L-amino acid peptides, D-amino acid peptides or diastereomeric peptides, to pharmaceutical compositions comprising same, and uses thereof in the treatment of infections and cancer diseases.

BACKGROUND OF THE INVENTION

The frequency of opportunistic fungal infections has increased in the last decade. Invasive mycoses have emerged as major causes of morbidity and mortality (Groll, A. H. et al. (1996) J. Infect. 33: 23-32; Minamoto, G. Y. and Rosenberg, A. S. (1997) Med. Clin. North Am. 81: 381-409; Walsh, T. J., et al. (1996) Infect. Dis. Clin. North Am. 10: 365-400). The vast majority of the invasive fungal infections are caused by *Aspergillus* and *Candida* species (Denning, D. W. (1991) J. Antimicrob. Chemother. 28: 1-16). As fungal cells have a restricted set of specific metabolic pathways and because of their eukaryotic nature, selective targeting of fungal cells has not been successfully achieved. Azoles that inhibit sterol formation and polyenes that bind to mature membrane sterols have been the mainstays of antifungal therapy for two decades or more. However, the development of fluconazole resistance among different pathogenic strains and the high toxicity of amphotericin B (Alexander, B. D. and Perfect, J. R. (1997) Drugs 54: 657-678) have prompted the search for new antifungal agents that can augment or replace therapeutic strategies for mycotic infections in the near future.

The investigation of antimicrobial peptides from a wide range of biological sources, and their synthetic derivatives, is a novel approach to new antifungal agents. Antimicrobial peptides are part of the innate immunity against microbial invasion in all organisms including human and plants and their possible mode of action has been reviewed in detail (Bechinger, B. (1999) Biochem. Biophys. Acta 1462: 157-183; Tossi, A., et al. (2000) Biopolymers 55: 4-30; Oren, Z. and Shai, Y. (1998) Biopolymers 47: 451-463). It is believed that most of these peptides bind and permeate the cell membranes. Antimicrobial peptides can be classified into two groups: (i) cell selective antimicrobial peptides that act on a narrow spectrum of microorganisms such as bacteria or fungi, and (ii) non-cell selective antimicrobial peptides that can lyse both microorganisms and normal mammalian cells.

One group of non-cell selective antimicrobial peptides includes native lipopeptides. These lipopeptides possess a broad spectrum of activities including antibacterial, antifungal, antiviral and cytolytic. Some of these lipopeptides are gene-encoded and synthesized ribosomally. However, some are synthesized non-ribosomally in bacteria, yeast, or fungi during cultivation on various carbon sources.

U.S. Pat. No. 6,183,736 describes the identification and purification of two lipopeptides from the culture medium of the bacteria *Bacillus subtilis*. Both lipopeptides are cyclic, acidic, and have a broad range of antifungal and antibacterial activity. It is disclosed that the two lipopeptides can be used for controlling aflatoxin-producing fungi contamination in plants. U.S. Pat. No. 6,384,013 discloses other antifungal lipopeptides, produced by culturing microorganisms. These are cyclic hexapeptides to which unique fatty acid acyl groups are attached. As a result of deacylation of the native acyl groups and reacylation with the unique acyl groups, the peptides exert enhanced antifungal and antiparasitic potency against pathogenic strains of fungi.

Recently, the present applicants incorporated several D-amino acids in the α-helical cytolytic peptides pardaxin and melittin (U.S. Pat. No. 6,172,038 and Shai, Y. and Oren, Z. (1996) J. Biol. Chem. 271: 7305-7308; Oren, Z., and Shai, Y. (1997) Biochemistry 36: 1826-1835). The resulting peptides of pardaxin and melittin having both L- and D-amino acids retained high antibacterial activity, while exhibiting reduced cytotoxic effects in mammalian cells. These peptides paved the way for the design of novel peptide antibiotics comprising both D- and L-amino acids that are selective to microorganisms.

U.S. Pat. No. 6,172,038 and WO 98/37090 disclose non-natural synthetic peptides comprising both L- and D-amino acid residues designated diastereomeric peptides with a net positive charge that is greater than +1. Some synthetic peptides consist of at least one hydrophobic amino acid and at least one positively charged amino acid, in which at least one of the amino acid residues is a D-amino acid. Several diastereomeric peptides containing from 6 to 30 amino acid residues are disclosed in U.S. Pat. No. 6,172,038 and WO 98/37090. Certain 12-mer peptides that contain lysine and a hydrophobic amino acid, in which one-third of the amino acid residues of the peptide are D-amino acid residues, were further investigated and found to be potent antimicrobial peptides having reduced hemolytic activity (Oren, Z., et al. (1997) J. Biol. Chem. 272: 14643-14649; Hong, J., et al. (1999) Biochemistry 38: 16963-16973; Avrahami, D., et al. (2001) Biochemistry 40: 12591-12603). WO 02/40529 discloses additional diastereomeric peptides having antibacterial, antifungal and anti-cancer activity.

In some studies investigators attached fatty acids to antimicrobial peptides in order to improve their properties, e.g., to increase their stability in serum and/or to reduce hemolytic activity (Efron, L., et al. (2002) J. Biol. Chem. 277: 24067-24072). In all of these studies, the investigated peptides had antimicrobial activity prior to the attachment of the fatty acids. In addition, it was shown that attachment of fatty acids to magainin, a well characterized α-helical, positively charged antimicrobial peptide, can endow it with antifungal activity (Avrahami, D., et al. (2002) Biochemistry 41: 2254-2263).

Lipopeptides capable of inducing immunological responses, particularly of cytotoxic T lymphocytes, have been disclosed in U.S. Pat. No. 5,871,746. The lipopeptides according to U.S. Pat. No. 5,871,746 comprise a peptide having between 10 to 40 amino acids and at least one antigenic determinant, particularly preferred are peptides derived from viral proteins.

U.S. Pat. No. 5,837,249 discloses methods for inducing a cytotoxic T cell response in a mammalian host against a viral infection comprising administering to the host a peptide-fatty acid conjugate, the peptide having the amino acid sequence corresponding to the amino acid sequence of a fragment of a glycoprotein or protein of virus.

U.S. Pat. No. 5,583,198 discloses compounds consisting of an amino acid or a peptide linked to a tromethamine derivative or ethanolamine derivative to which one or more fatty acids are optionally linked. The fatty acids according to U.S. Pat. No. 5,583,198 may enhance the immunogenic properties of the peptides, enhance their absorption, and provide slow-release delivery.

Nowhere in the background art is it disclosed or suggested that coupling of fatty acids to positively charged peptides that are inactive or weakly active antibacterial and/or antifungal peptides may impart to the conjugates antibacterial and/or antifungal activity as well as endow the conjugates with selective cytolytic activity against tumor cells.

SUMMARY OF THE INVENTION

The present invention provides safe and effective antimicrobial compositions. Particularly, the present invention provides compositions that can be used against a broad range of microbes including bacteria and fungi. The compositions of the invention reduce or even eliminate the need of using antibiotics, and therefore do not promote the growth of antibiotic-resistant bacteria strains as may occur when antibiotics are being used. The present invention further relates to anticancer compositions that do not contain harsh or toxic chemicals. The compositions are particularly useful for pharmaceutical applications, especially for topical treatment of microbial infections as well as for treatment of cancer. The compositions are also useful for hygiene and sanitation, as disinfectants, for food preservation, and for agricultural use.

It is now disclosed that conjugation of a lipophilic moiety, particularly a fatty acid, to an otherwise inactive or weakly active antimicrobial and/or anticancer peptide can unexpectedly endow the peptide with superior antimicrobial activity and/or selective cytolytic activity against tumor cells.

According to one aspect, the present invention provides a lipophilic conjugate comprising a peptide coupled to a fatty acid, the peptide having a net positive charge that is equal or greater than +1 comprising at least two positively charged amino acid residues, said peptide after conjugation to the fatty acid having at least one activity selected from the group consisting of antibacterial, antifungal, and anticancer activity, wherein the activity after conjugation being higher than prior to conjugation, a cyclic analog, or a salt thereof. In a current preferred embodiment, the net positive charge of the peptide is greater than +1.

The terms "lipophilic conjugate" and "lipopeptide" used interchangeably throughout the specification and claims designate a conjugate comprising a peptide covalently coupled to a fatty acid.

According to one embodiment of the invention, the peptide consists of at least two amino acid residues. According to currently preferred embodiments, the peptide consists of 3 to 15 amino acid residues. A lipopeptide comprising at least one positively charged amino acid is also encompassed in the present invention.

It will be understood that the present invention encompasses lipophilic conjugates in which the peptide moiety has overall low hydrophobicity so that the peptide alone (without the fatty acid) does not significantly perturb phospholipid membranes and thus does not kill microorganisms. Conjugates comprising the model diastereomeric peptides disclosed in U.S. Pat. No. 6,172,038, WO 98/37090 and in WO 02/40529 are explicitly incorporated by reference as if fully set forth herein. Thus, the present invention relates to known as well as novel peptides that are devoid or possess very weak antimicrobial and/or anticancer activity when not conjugated to a fatty acid in accordance with the principles of the invention.

The present invention also provides shorter peptides than those disclosed in the background art, inasmuch as the known antimicrobial diastereomeric peptides disclosed in the art have a minimal length of six amino acids. According to the principles of the present invention the conjugation of a fatty acid can impart antimicrobial and/or anticancer properties to peptides as short as di- or tri-peptides.

Typically, an inactive antimicrobial peptide is defined as a peptide of which a concentration higher than 100 μM is required to significantly inhibit bacteria and/or fungi growth. A peptide having low or weak antimicrobial activity is defined as a peptide of which a concentration between 25 to 100 μM is required to significantly inhibit bacteria and/or fungi growth. Active antimicrobial peptide is defined as a peptide of which a concentration between 10 to 25 μM is required to significantly inhibit bacteria and/or fungi growth. Highly active antimicrobial peptide is defined as a peptide of which a concentration between 5 to 10 μM is required to significantly inhibit bacteria and/or fungi growth, and very highly active antimicrobial peptide is defined as a peptide of which a concentration lower than 5 μM is required to significantly inhibit bacteria and/or fungi growth.

According to the present invention, an inactive anticancer peptide is defined as a peptide of which the LC50 (the concentration at which 50% of the cells die) is higher than 50 μM. A peptide having low or weak anticancer activity is defined as a peptide of which the LC50 is between 25 to 50 μM. Active anticancer peptide is defined as a peptide of which the LC50 is between 10 to 25 μM. Highly active anticancer peptide is defined as a peptide of which the LC50 is between 5 to 10 μM, and very highly active anticancer peptide is defined as a peptide of which the LC50 is lower than 5 μM. The LC50 is determined in an in-vitro assay.

According to the principles of the present invention, the peptide prior to conjugation of a fatty acid is either inactive or weakly active antibacterial and/or antifungal and/or anticancer agent. Conjugation of the fatty acid endows the peptide with at least one activity selected from antibacterial, antifungal, and anticancer activity so that said activity is significantly higher after conjugation than prior to conjugation. Preferably, conjugation of a fatty acid to a peptide of the invention enhances at least one activity selected from antibacterial, antifungal, and anticancer activity by at least 2 fold, more preferably by at least 10 fold, and most preferably by at least 20 fold. It will be appreciated that by referring to endowment of a peptide with antibacterial and/or antifungal and/or anticancer activity, this is not intended to imply that the activity affects all bacteria or fungi species nor all cancer cell types. It is to be understood that the activity imparted to the previously inactive or weakly active peptide upon conjugation of a fatty acid to said peptide implies that at least one bacterial species or fungal species or cancer cell type is susceptible to this activity.

The peptides of the present invention comprise L-amino acids, D-amino acids, or combinations thereof. The amino acids may be selected from natural and non-natural amino acids. Peptides having both D-amino acid residues and L-amino acid residues are defined herein as diastereomeric peptides. Typically, the D-amino acid residues constitute at least one third of the amino acids of a diastereomeric peptide. The location of the D-amino acid residues may vary so long as the antimicrobial and/or anticancer activity of the conjugate is retained. In a currently preferred embodiment, the D-amino acid residues are located 1 to 4 amino acid residues apart.

According to another embodiment of the invention, the fatty acid is selected from the group consisting of saturated, unsaturated, monounsaturated, and polyunsaturated fatty acids. According to currently preferred embodiments, the fatty acids consist of at least eight carbon atoms. Examples of the fatty acids that may be coupled to the peptides of the invention include, but are not limited to, decanoic acid (DA), undecanoic acid (UA), dodecanoic acid (DDA; lauric acid), myristic acid (MA), palmitic acid (PA), stearic acid, arachidic acid, lignoceric acid, palmitoleic acid, oleic acid, linoleic acid, linolenic acid, arachidonic acid, trans-hexadecanoic acid, elaidic acid, lactobacillic acid, tuberculostearic acid, and cerebronic acid. According to currently more preferred embodiments, the fatty acid is selected from decanoic acid, undecanoic acid, dodecanoic acid, myristic acid, and palmitic acid.

The fatty acid may be coupled to the N-terminal of the peptide, to the C-terminal, or to any other free functional group along the peptide chain, for example, to the ε-amino group of lysine. According to certain currently preferred embodiments, the fatty acid is coupled to the N-terminus of the peptide.

According to a further embodiment, the lipophilic conjugate comprises a fatty acid coupled to a lysine dipeptide, tripeptide, or tetrapeptide. Examples of such conjugates are the lipopeptides of SEQ ID NOS: 1 to 3:

```
                                          SEQ ID No:1
Palmitoyl-Lys-D-Lys-NH2

SEQ ID No:2
Palmitoyl-Lys-Lys-Lys-NH2

SEQ ID No:3
Palmitoyl-Lys-D-Lys-Lys-NH2
```

It should be understood that the fatty acid may be varied and the lipopeptides disclosed are non-limitative exemplary embodiments.

According to another embodiment, the lipophilic conjugate comprises a peptide coupled to a fatty acid, the peptide comprising at least two positively charged amino acids selected from lysine, arginine, histidine, or a combination thereof, and a hydrophobic amino acid selected from Gly, Ala, Leu, Ile, Val, or a combination thereof.

According to a further embodiment, the lipopeptide comprises at least two Lys residues as the positively charged amino acids and the hydrophobic amino acid is selected from Gly, Ala, Leu, Ile, or Val. Examples of such conjugates are 3-, 4-, 6-9-, 11 and 12-mer lipopeptides of SEQ ID NOS: 4 to 24:

```
                                          SEQ ID NO:4
Palmitoyl-Lys-Gly-Gly-D-Lys-NH2

SEQ ID NO:5
Palmitoyl-Lys-Leu-D-Leu-Lys-NH2

SEQ ID NO:6
Palmitoyl-Lys-Ala-D-Ala-Lys-NH2

SEQ ID NO:7
Palmitoyl-Lys-D-Leu-D-Leu-Leu-Lys-Leu-NH2

SEQ ID NO:8
Palmitoyl-Lys-D-Ile-D-Ile-Ile-Lys-Ile-NH2

SEQ ID NO:9
Palmitoyl-Lys-D-Val-D-Val-Val-Lys-Val-NH2

SEQ ID NO:10
Palmitoyl-Lys-D-Ala-D-Ala-Ala-Lys-Ala-NH2
```

```
                                          SEQ ID NO:11
Palmitoyl-D-Lys-Gly-Gly-Gly-D-Lys-Gly-NH2

SEQ ID NO:12
Palmitoyl-Lys-Leu-D-Leu-Lys-Leu-Leu-D-Lys-D-Lys-
Leu-NH2

SEQ ID NO:13:
Palmitoyl-Leu-Lys-D-Leu-Leu-Lys-D-Lys-Leu-D-Leu-D-
Lys-Lys-Leu-NH2

SEQ ID NO:14:
Myristoyl-D-Lys-Gly-Gly-Gly-D-Lys-Gly-Gly-Gly-D-
Lys-Gly-Gly-D-Lys-NH2

SEQ ID NO:15:
Palmitoyl-D-Lys-Gly-Gly-Gly-D-Lys-Gly-Gly-Gly-D-
Lys-Gly-Gly-D-Lys-NH2

SEQ ID NO:16:
Palmitoyl-Lys-Ala-D-Ala-D-Ala-Lys-Ala-Ala-D-Ala-
Lys-D-ALa-Ala-Lys-NH2

SEQ ID NO:17:
Palmitoyl-Lys-Val-D-Val-D-Val-Lys-Val-Val-D-Val-
Lys-D-Val-Val-Lys-NH2

SEQ ID NO:18:
Palmitoyl-Lys-Ile-D-Ile-D-Ile-Lys-Ile-Ile-D-Ile-
Lys-D-Ile-Ile-Lys-NH2

SEQ ID NO:19:
Undecanoyl-Lys-Leu-D-Leu-D-Leu-Lys-Leu-Leu-D-Leu-
Lys-D-Leu-Leu-Lys-NH2

SEQ ID NO:20:
Palmitoyl-Lys-Leu-D-Leu-D-Leu-Lys-Leu-Leu-D-Leu-
Lys-D-Leu-Leu-Lys-NH2

SEQ ID NO:21:
Decanoyl-D-Leu-Lys-Lys-D-Leu-D-Leu-Lys-Lys-D-Leu-
D-Leu-Lys-Lys-D-Leu-NH2

SEQ ID NO:22:
Dodecanoyl-D-Leu-Lys-Lys-D-Leu-D-Leu-Lys-Lys-D-
Leu-D-Leu-Lys-Lys-D-Leu-NH2

SEQ ID NO:23:
Myristoyl-D-Leu-Lys-Lys-D-Leu-D-Leu-Lys-Lys-D-Leu-
D-Leu-Lys-Lys-D-Leu-NH2

SEQ ID NO:24:
Palmitoyl-D-Leu-Lys-Lys-D-Leu-D-Leu-Lys-Lys-D-Leu-
D-Leu-Lys-Lys-D-Leu-NH2
```

According to another embodiment, the lipopeptide comprises at least two arginine or histidine residues as the positively charged amino acids and leucine as the hydrophobic amino acid. Examples of such conjugates are lipopeptides of SEQ ID NO: 25 to 27:

```
                                      SEQ ID NO:25:
Palmitoyl-Arg-Leu-D-Leu-Arg-NH₂

SEQ ID NO:26:
Dodecanoyl-D-Leu-Arg-Arg-D-Leu-D-Leu-Arg-Arg-D-
Leu-D-Leu-Arg-Arg-D-Leu-NH₂

SEQ ID NO:27:
Dodecanoyl-D-Leu-His-His-D-Leu-D-Leu-His-His-D-
Leu-D-Leu-His-His-D-Leu-NH₂
```

According to a further embodiment, the lipopeptide comprises leucine as the hydrophobic amino acid and a combination of at least two positively charged amino acids selected from the group consisting of lysine, arginine, and histidine. Examples of such conjugates are lipopeptides of SEQ ID NOS: 28 to 33:

```
                                      SEQ ID NO:28:
Palmitoyl-Lys-Leu-D-Leu-Arg-Leu-Leu-D-Lys-D-Lys-
Leu-D-Leu-Arg-NH₂

SEQ ID NO:29:
Palmitoyl-Lys-Leu-D-Leu-Leu-Arg-D-Leu-Leu-D-Lys-
D-Lys-Leu-Leu-Arg-NH₂

SEQ ID NO:30:
Palmitoyl-Lys-Leu-D-Leu-Arg-Leu-Leu-D-Lys-D-Lys-
Leu-D-Leu-Arg-Leu-NH₂

SEQ ID NO:31:
Palmitoyl-Lys-Leu-D-Leu-Leu-Arg-D-Leu-Leu-D-Lys-
D-Lys-Leu-Leu-Arg-D-Leu-Lys-NH₂

SEQ ID NO:32:
Dodecanoyl-D-Leu-Arg-His-D-Leu-D-Leu-Arg-His-D-
Leu-D-Leu-Arg-His-D-Leu-NH₂

SEQ ID NO:33:
Dodecanoyl-D-Leu-Lys-His-D-Leu-D-Leu-Lys-His-D-
Leu-D-Leu-Lys-His-D-Leu-NH₂
```

According to another embodiment, the lipopeptide comprises at least two positively charged amino acids and a combination of hydrophobic and/or non-hydrophobic amino acids. In one particular embodiment, the hydrophobic and non-hydrophobic amino acids are selected from Leu, Gly, Ala, Ser, Thr, and Met, and examples thereof are the 7-mer lipopeptides of SEQ ID NOS: 34 to 35:

```
                                      SEQ ID NO:34
Palmitoyl-Leu-D-Leu-Leu-Arg-D-Leu-Gly-Leu-NH₂

SEQ ID NO:35
Palmitoyl-Leu-D-Leu-Lys-Leu-Leu-D-Lys-Gly-NH₂
```

According to a further embodiment, the conjugate comprises a peptide comprising at least two positively charged amino acids and a negatively charged amino acid. In a currently preferred embodiment, the positively charged amino acid is lysine. Examples of such conjugates are the 3- and 4-mer lipopeptides of SEQ ID NOS: 36 to 38:

```
                                      SEQ ID NO:36
Palmitoyl-Glu-Lys-D-Lys-Lys-NH₂

SEQ ID NO:37
Palmitoyl-Lys-D-Lys-Glu-Lys-NH₂

SEQ ID NO:38
Palmitoyl-Glu-D-Lys-Lys-NH₂
```

According to still a further embodiment, the invention relates to cyclic analogs of the lipophilic conjugates. Examples of such cyclic conjugates are the lipopeptides of SEQ ID NO: 39 to 46:

```
                                                                      SEQ ID NO:39
             ┌──────────────────────────────────────┐
Palmitoyl-Cys-Lys-D-Leu-D-Leu-Leu-Lys-Leu-Cys-NH₂

SEQ ID NO:40
             ┌──────────────────────────────────────┐
Palmitoyl-Cys-Lys-D-Ala-D-Ala-Ala-Lys-Ala-Cys-NH₂

SEQ ID NO:41
             ┌──────────────────────────────────────┐
Palmitoyl-Cys-D-Lys-Gly-Gly-Gly-D-Lys-Gly-Cys-NH₂

SEQ ID NO:42:
             ┌──────────────────────────────────────────────────────┐
Palmitoyl-Cys-Lys-D-Ile-D-Ile-Ile-Lys-Ile-Ile-D-Ile-Lys-D-Ile-Ile-Lys-Cys-NH₂

SEQ ID NO:43:
             ┌──────────────────────────────────────────────────────┐
Palmitoyl-Cys-Lys-Ala-D-Ala-D-Ala-Lys-Ala-Ala-D-Ala-Lys-D-Ala-Ala-Lys-Cys-NH₂

SEQ ID NO:44:
             ┌──────────────────────────────────────────────────────┐
Myristoyl-Cys-Lys-Ala-D-Ala-D-Ala-Lys-Ala-Ala-D-Ala-Lys-D-Ala-Ala-Lys-Cys-NH₂

SEQ ID NO:45
             ┌──────────────────────────────────────────────────────┐
Myristoyl-Cys-D-Lys-Gly-Gly-Gly-D-Lys-Gly-Gly-Gly-D-Lys-Gly-Gly-D-Lys-Cys-NH₂
```

-continued

SEQ ID NO:46:

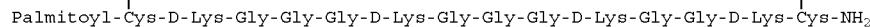

Palmitoyl-Cys-D-Lys-Gly-Gly-Gly-D-Lys-Gly-Gly-Gly-D-Lys-Gly-Gly-D-Lys-Cys-NH$_2$ According to another aspect, the present invention provides a pharmaceutical composition comprising as an active ingredient a lipophilic conjugate comprising a peptide coupled to a fatty acid, the peptide having a net positive charge that is equal or greater than +1 comprising at least two positively charged amino acid residues, said peptide after conjugation to the fatty acid having at least one activity selected from the group consisting of antibacterial, antifungal, and anticancer activity, wherein the activity after conjugation being higher than prior to conjugation, a cyclic analog, or a salt thereof.

The pharmaceutical composition may be formulated for any route of administration including, but not limited to, intravenous, intramuscular, intraperitoneal, nasal, oral, intralesional and topical. In currently preferred embodiments, the pharmaceutical composition is formulated for topical or intralesional administration.

According to a further aspect, the present invention provides a composition comprising as an active ingredient a lipophilic conjugate of the invention useful for hygienic purposes, as a disinfectant, for food preservation, for veterinary use, or for agricultural use.

According to a further aspect, the present invention provides a method for treating an infection caused by pathogenic organisms in a subject comprising administering to a subject in need thereof a therapeutically effective amount of a pharmaceutical composition comprising a lipophilic conjugate of the invention and a pharmaceutically acceptable carrier.

Infections that may be treated by the pharmaceutical composition of the invention include, but are not limited to, topical infections caused by pathogenic organisms such as bacterial infections, particularly infections caused by bacteria resistant to antibiotics, and infections caused by pathogenic fungi.

According to a further aspect, the present invention provides a method for treating cancer in a subject comprising administering to a subject in need thereof a therapeutically effective amount of a pharmaceutical composition comprising a lipophilic conjugate of the invention and a pharmaceutically acceptable carrier.

According to one embodiment, cancers that may be treated by the pharmaceutical compositions of the invention include benign and malignant solid or non-solid tumors.

In a further aspect, the present invention provides a method for disinfecting an object comprising contacting an object with a microbicidally effective amount of a disinfecting composition comprising as an active ingredient a lipophilic conjugate of the invention.

These and other embodiments of the present invention will be better understood in relation to the description, figures, examples, and claims that follow.

DETAILED DESCRIPTION OF THE INVENTION

Figure 1:
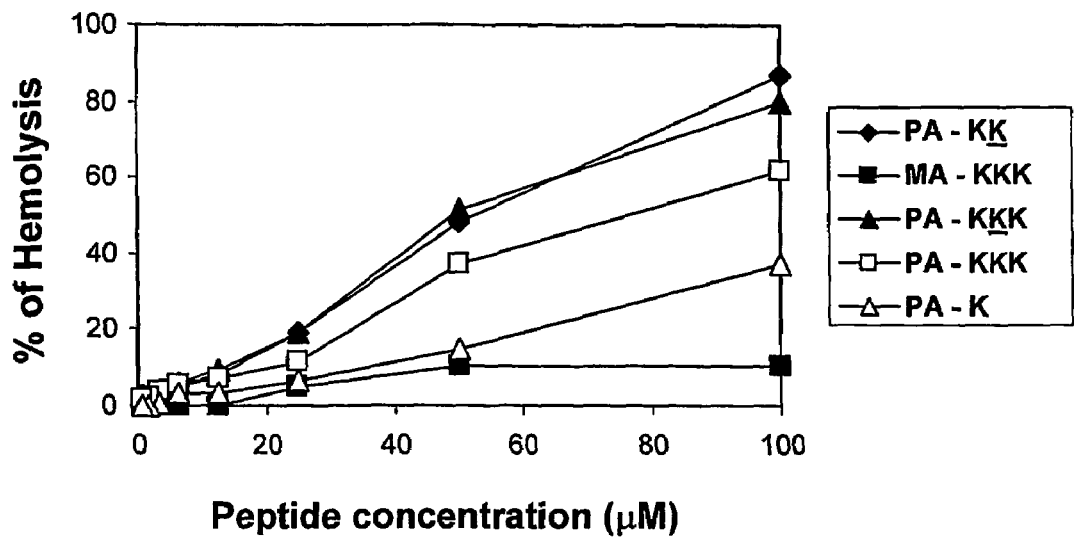
FIG. 1 shows the lack of hemolytic activity of short lipopeptides having 1 to 3 amino acid residues at concentrations lower than 25 µM, concentrations at which the lipopeptides exert antimicrobial activity. Human red blood cells were incubated in the presence of increasing concentrations of the lipopeptides for 1 h, and the release of hemoglobin was monitored by measuring the absorbance at 540 nm.
Figure 2:
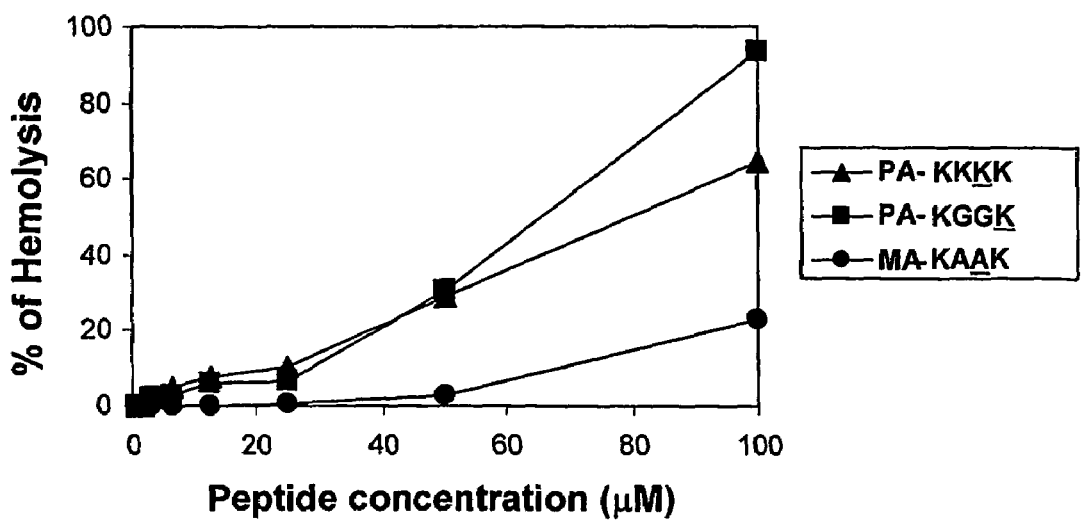
FIG. 2 shows the lack of hemolytic activity of short lipopeptides having 4 amino acid residues at concentrations lower than 25 µM, concentrations at which the lipopeptides exert antimicrobial activity. The hemolytic activity was monitored by measuring the absorbance at 540 nm.
Figure 3:
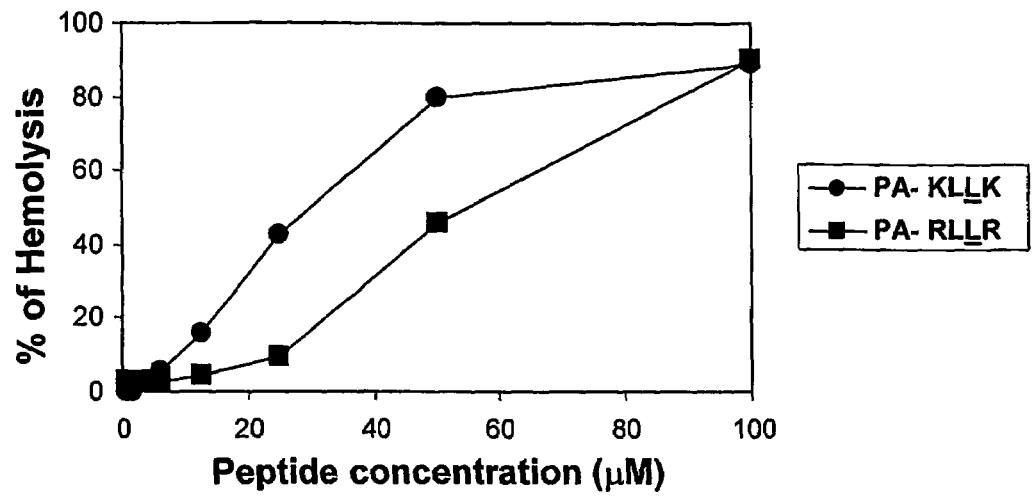
FIG. 3 shows the lack of hemolytic activity of additional short lipopeptides having 4 amino acid residues at concentrations lower than 12.5 µM, concentrations at which the lipopeptides exert antimicrobial activity. The hemolytic activity was monitored by measuring the absorbance at 540 nm.
Figure 4:
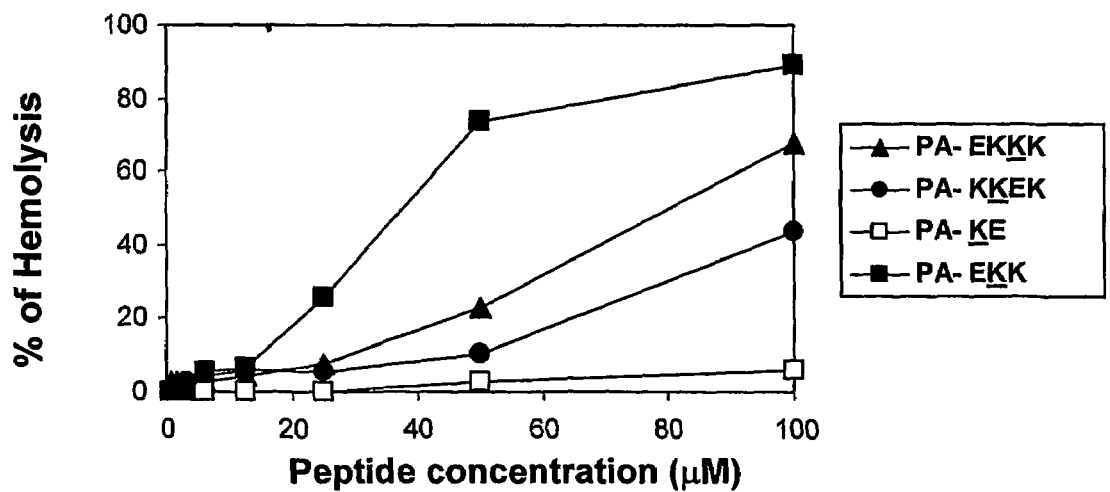
FIG. 4 shows the lack of hemolytic activity of short lipopeptides having 2 to 4 amino acid residues at concentrations lower than 12.5 µM, concentrations at which the lipopeptides exert antimicrobial activity. The hemolytic activity was monitored by measuring the absorbance at 540 nm.
Figure 5:
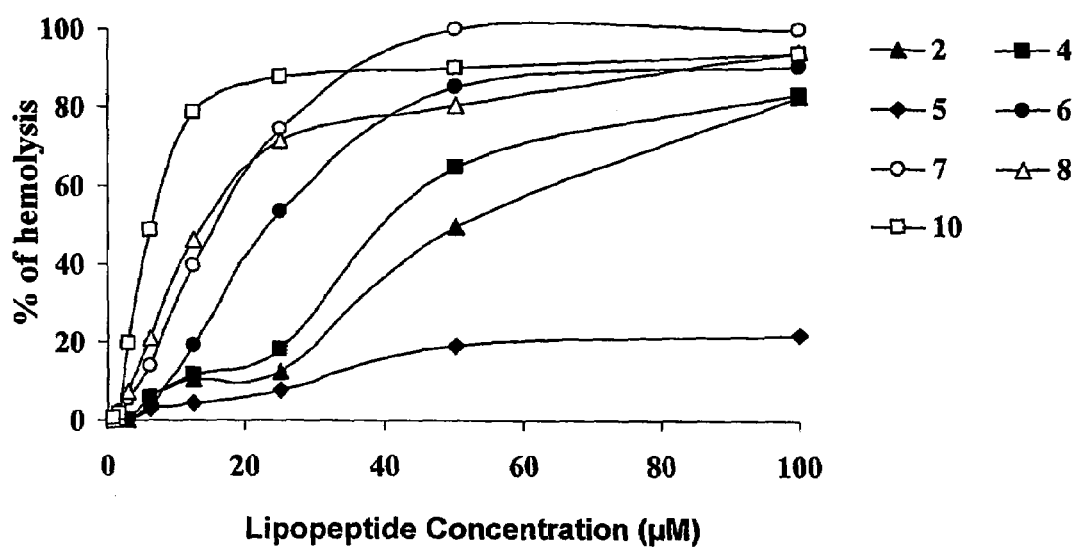
FIG. 5 shows the hemolytic activity of lipopeptides having 12 amino acid residues. Note that at concentrations lower than 12.5 µM, lipopeptides 2, 4, and 5 were not hemolytic, and at concentrations lower than 5 µM, peptides 6 to 8 were not hemolytic. The hemolytic activity was monitored by measuring the absorbance at 540 nm.

Diastereomeric peptides, which have been shown to be active against bacteria, have a narrow spectrum of activity against fungi, especially against filamentous fungi. In order to improve the cytolytic activity of L-amino acid peptides or of diastereomeric peptides against fungi, or to modify an inactive peptide such that it will be active against fungi and/or bacteria and/or tumor cell, fatty acids (having variable lengths) were attached to the peptides at either the N-terminus, the C-terminus, or along the peptide chain. Several parameters such as the length of the peptide, the location and number of D-amino acids, the polarity of the diastereomeric peptide, and the length of the fatty acid were found to affect the peptide potency, selectivity and spectrum of activity towards pathogenic cells such as bacteria, fungi, and cancer cells.

Due to the increased structural and sequence flexibility of the lipopeptides of the invention, this family of lipopeptides provides an efficient alternative to the known native amphipathic α-helical antimicrobial peptides having a complex sequence of hydrophobic and polar amino acid residues, and hence provides important advantages for the design of a repertoire of potent anti-pathogenic lipopeptides for the treatment of diseases.

The present invention provides lipophilic conjugates comprising a peptide coupled to a fatty acid, the peptide having a net positive charge that is equal or greater than +1 comprising at least two positively charged amino acid residues, said peptide after conjugation to the fatty acid having at least one activity selected from the group consisting of antibacterial, antifungal, and anticancer activity, wherein the activity after conjugation being higher than prior to conjugation, a cyclic analog, or a salt thereof. Preferably, the net positive charge of the peptide is greater than +1.

The term "diastereomeric peptide" as used herein refers to a peptide comprising both L-amino acid residues and D-amino acid residues. The amino acid residues are represented throughout the specification and claims by three-letter codes according to IUPAC conventions. When there is no indication, the amino acid residue occurs in L isomer configuration. Amino acid residues present in D isomer configuration are indicated by "D" before the residue abbreviation.

The term "antimicrobial activity" as used herein refers to lytic activity against microorganisms. Particularly, the antimicrobial activity refers to antifungal activity and/or antibacterial activity. However, activity against other pathogenic organisms such as viruses, mycoplasma, and protozoa is also contemplated in the present invention.

The term "anticancer activity" as used herein refers to preferential cytotoxic effect against tumor cells without any significant adverse effects to normal cells under the same conditions of exposure. It will be understood that the enhanced cytotoxic effect of the lipophilic conjugates of the invention against tumor cells compared to normal cells depends primarily upon the metabolic activity of the cells. Thus, while tumor cells proliferate at high rates and hence have increased metabolic activity, these cells are more affected by the lipophilic conjugates of the invention, whereas normal cells, which typically exhibit lower metabolic activity compared to tumor cells, are less affected by the lipophilic conjugates of the invention. The cytotoxic effect under in vitro or in vivo conditions is detected by various means known in the art, for example, by measuring thymidine incorporation into cells, by metabolic assays using MTT, XTT, or AlamarBlue fluorescent reagents, and by gadolinium enhanced MRI scanning.

Typically, an inactive antimicrobial peptide is defined as a peptide of which a concentration higher than 100 µM is required to significantly inhibit bacteria and/or fungi growth. A peptide having low antimicrobial activity is defined as a peptide of which a concentration between 25 to 100 µM is required to significantly inhibit bacteria and/or fungi growth. Active peptide is defined as a peptide of which a concentration between 10 to 25 µM is required to significantly inhibit bacteria and/or fungi growth. Highly active peptide is defined as a peptide of which a concentration between 5 to 10 µM is required to significantly inhibit bacteria and/or fungi growth, and very highly active peptide is defined as a peptide of which a concentration lower than 5 µM is required to significantly inhibit bacteria and/or fungi growth.

Typically, an inactive anticancer peptide is defined as a peptide of which the LC50 (the concentration at which 50% of the cells die) is higher than 50 µM. A peptide having low or weak anticancer activity is defined as a peptide of which the LC50 is between 25 to 50 µM. Active anticancer peptide is defined as a peptide of which the LC50 is between 10 to 25 µM. Highly active anticancer peptide is defined as a peptide of which the LC50 is between 5 to 10 µM, and very highly active anticancer peptide is defined as a peptide of which the LC50 is lower than 5 M. The LC50 is determined in an in-vitro assay.

The terms "lipopeptide" and "lipophilic conjugate" as used herein refer to a peptide covalently coupled to a fatty acid. The terms lipopeptide and lipophilic conjugate are used interchangeably throughout the specification and claims.

The lipopeptide of the invention comprises at least two amino acid residues. In currently preferred embodiments, the lipopeptides comprise 3-15 amino acid residues. However, a lipopeptide comprising at least one positively charged amino acid is also contemplated in the invention. It should be understood that lipopeptides in which the peptide moiety has overall low hydrophobicity that does not allow the peptide alone (without the fatty acid) to perturb phospholipid membranes and to kill microorganisms are contemplated in the invention.

The peptides of the present invention can be synthesized using methods well known in the art including chemical synthesis and recombinant DNA technology. Synthesis may be performed by solid phase peptide synthesis described by Merrifield (see J. Am. Chem. Soc., 85:2149, 1964). Alternatively, the peptides of the present invention can be synthesized using standard solution methods (see, for example, Bodanszky, M., Principles of Peptide Synthesis, Springer-Verlag, 1984). Preferably, the peptides of the invention are synthesized by solid phase peptide synthesis as exemplified herein below (Example 1). Cyclization of the lipopeptides of the invention can be performed by methods known in the art, for example, by inserting two cysteine residues or analogs thereof to form a disulfide bond (see Examples herein below and Unger et al. (2001) Biochemistry 40: 6388-6397). Cyclization may also be performed between the carboxyl and amino termini of the peptide. Alternatively or additionally, cyclization may be performed between a functional group of an amino acid, for example an ε-amino group of Lys, and the carboxyl terminus of the peptide (see Examples herein below and Tsubery et al., (2000) J. Med. Chem. 43: 3085-3092). Thus, the present invention encompasses any cyclic analog of linear peptides disclosed in the present invention.

The invention contemplates lipophilic conjugates comprising peptides composed of natural amino acids, non-natural amino acids, and analogs thereof. Examples of non-natural amino acids are norleucine, ornithine, citrulline, diaminobutyric acid, homoserine, isopropyl Lys, 3-(2'-naphtyl)-Ala, nicotinyl Lys, amino isobutyric acid, and 3-(3'-pyridyl-Ala). The net positive charge of a peptide of the invention is due to the amino acid composition of the peptide, but derivatization of non-charged amino acid residues to yield positively charged amino acids as known in the art, for example by methylation, is contemplated in the present invention.

Positively charged amino acids as used herein are selected from positively charged amino acids known in the art. Examples of positively charged amino acids are lysine, arginine, and histidine. Hydrophobic amino acids as used herein are selected from hydrophobic amino acids known in the art. Examples of hydrophobic amino acids are leucine, isoleucine, glycine, alanine, and valine. Negatively charged amino acids are selected from negatively charged amino acids known in the art including, but not limited to, glutamic acid and aspartic acid.

The fatty acid that can be coupled to the peptides of the invention is selected from saturated, unsaturated, monounsaturated, and polyunsaturated fatty acids. Typically, the fatty acid consists of at least eight carbon atoms, such as, for example, decanoic acid (DA), undecanoic acid (UA), dodecanoic acid (lauric acid), myristic acid (MA), palmitic acid (PA), stearic acid, arachidic acid, lignoceric acid, palmitoleic acid, oleic acid, linoleic acid, linolenic acid, arachidonic acid, trans-hexadecanoic acid, elaidic acid, lactobacillic acid, tuberculostearic acid, and cerebronic acid. The fatty acid may be coupled to the N-terminal, to the C-terminal, or to any other free functional group along the peptide chain, for example, to the ε-amino group of lysine. Coupling of a fatty acid to a peptide is performed similarly to the coupling of an amino acid to a peptide during peptide synthesis (Examples herein below). It should be understood that the fatty acid is covalently coupled to the peptide. The terms "coupling" and "conjugation" are used herein interchangeably and refer to the chemical reaction, which results in covalent attachment of a fatty acid to a peptide to yield a lipophilic conjugate.

According to some embodiments of the invention, a short peptide (2- to 4-mer peptide) is coupled to a long aliphatic chain fatty acid while a long peptide, e.g., 12-mer peptide, is coupled to a short aliphatic chain fatty acid. Thus, for example, a peptide consisting of from two to four amino acid residues and having little or no antimicrobial activity at concentrations below 25 μM is coupled to a fatty acid that consists of at least 16 carbon atoms such as, for example, palmitic acid. Also, a peptide consisting of at least five amino acid residues is coupled to a fatty acid having at least 10 carbon atoms such as, for example, undecanoic acid or myristic acid. However, it should be understood that any fatty acid having at least eight carbon atoms could be coupled to the peptides of the invention so long as the antimicrobial and/or anticancer activity of the conjugate is enhanced. Though we do not wish to be bound to any mechanism of action, it will be appreciated that coupling of a fatty acid to a peptide is aimed at increasing peptide hydrophobicity, optionally its oligomerization in solution, and thus endowing it with antimicrobial and/or anticancer activity.

The present invention provides pharmaceutical compositions comprising the lipophilic conjugates of the invention and a cosmetically and/or pharmaceutically acceptable carrier. The term "pharmaceutically acceptable carrier" refers to a vehicle which delivers the active components to the intended target and which does not cause harm to humans or other recipient organisms. As used herein, "pharmaceutical" will be understood to encompass both human and animal pharmaceuticals. Useful carriers include, for example, water, acetone, ethanol, ethylene glycol, propylene glycol, butane-1,3-diol, isopropyl myristate, isopropyl palmitate, or mineral oil. Methodology and components for formulation of pharmaceutical compositions are well known, and can be found, for example, in Remington's Pharmaceutical Sciences, Eighteenth Edition, A. R. Gennaro, Ed., Mack Publishing Co. Easton Pa., 1990. The pharmaceutical composition may be formulated in any form appropriate to the mode of administration, for example, solutions, colloidal dispersions, emulsions (oil-in-water or water-in-oil), suspensions, creams, lotions, gels, foams, sprays, aerosol, ointment, tablets, suppositories, and the like.

The pharmaceutical compositions can also comprise other optional materials, which may be chosen depending on the carrier and/or the intended use of the composition. Additional components include, but are not limited to, antioxidants, chelating agents, emulsion stabilizers, e.g., carbomer, preservatives, e.g., methyl paraben, fragrances, humectants, e.g., glycerin, waterproofing agents, e.g., PVP/Eicosene Copolymer, water soluble film-formers, e.g., hydroxypropyl methylcellulose, oil-soluble film formers, cationic or anionic polymers, and the like.

The pharmaceutical compositions useful in the practice of the present invention comprise a lipopeptide of the invention optionally formulated into the pharmaceutical composition as a pharmaceutically acceptable salt form. Pharmaceutically acceptable salts include the acid addition salts (formed with the free amino groups of the polypeptide), which are formed with inorganic acids, such as for example, hydrochloric or phosphoric acid, or with organic acids such as acetic, oxalic, tartaric, and the like.

Suitable bases capable of forming salts with the lipopeptides of the present invention include, but are not limited to, inorganic bases such as sodium hydroxide, ammonium hydroxide, potassium hydroxide and the like; and organic bases such as mono-, di- and tri-alkyl and aryl amines (e.g. triethylamine, diisopropyl amine, methyl amine, dimethyl amine and the like) and optionally substituted ethanolamines (e.g. ethanolamine, diethanolamine and the like).

The lipophilic conjugates of the invention can be used individually or in combination with other components for disinfecting objects. The term "disinfecting" relates to preventing, inhibiting, and/or alleviating microbial growth, and is used interchangeably with sterilizing. The amount of each component used will depend on the purpose of the use, e.g., disinfecting medical or surgical equipment, and disinfecting tissue culture equipment, media, incubators, hoods, dishes, and the like. The compositions may also be used for treating contact lenses, such as disinfecting solutions, cleaning products and products for enhancing the ocular comfort of patients wearing contact lenses; other types of ophthalmic compositions, such as ocular lubricating products, artificial tears, and the like. The concentration determined to be necessary for the above-stated purposes can be functionally described as "an amount effective to disinfect" or "microbicidally effective amount" or variations thereof.

The lipopeptides of the invention may also be used for food preservation, in veterinary compositions as alternative to antibiotics, or for agricultural use.

The present invention provides methods for treating an infection in a subject comprising administering to the subject a therapeutically effective amount of a pharmaceutical composition comprising a lipophilic conjugate of the invention and a pharmaceutically acceptable carrier.

The present invention also provides methods for treating cancer in a subject comprising administering to the subject a therapeutically effective amount of a pharmaceutical composition comprising a lipophilic conjugate of the invention and a pharmaceutically acceptable carrier.

As used herein, the term "treating" means remedial treatment, and encompasses the terms "reducing", "suppressing", "ameliorating" and "inhibiting", which have their commonly understood meaning of decreasing or arresting an infection and/or decreasing or arresting tumor growth.

The term "therapeutically effective amount" as used herein refers to an amount of the pharmaceutical composition that when administered to a subject is capable of exerting antifungal and/or antibacterial and/or anticancer activity. Assays for detecting the antifungal and/or antibacterial and/or anticancer activity are well known in the art and include, but are not limited to, in vitro assays for bacterial growth, fungal growth, and tumor cell growth as described herein below (Examples 3, 4, and 7 herein below). Thus, according to the present invention, a therapeutically effective amount is an amount that when administered to a subject is sufficient to inhibit, preferably to eradicate, bacterial and/or fungal infection and/or cancer growth. According to the present invention, a subject is an animal, preferably a mammal, and more preferably a human.

According to the present invention, the step of administering the pharmaceutical compositions of the invention includes any route of administration including, but not limited to, intravenous, intraarterial, intramuscular, intraperitoneal, oral, ophthalmic, nasal, vaginal, rectal, intralesional, and topical. Particularly, the pharmaceutical compositions of the invention are useful for topical and intralesional application. As used herein, the term "topical" means "pertaining to a particular surface area" and the topical agent applied to a certain area of said surface will affect only the area to which it is applied. Thus, any and all applications in which the lipophilic conjugates act locally and not through the blood circulation are also encompassed in the present invention. It should be also appreciated that local administration of the pharmaceutical compositions of the invention directly into a tumor or adjacent to the tumor are highly useful.

The lipopeptides of the invention may be used in topical applications against a wide variety of topical infections. Such applications include, but are not limited to, treatment of bacterial and fungal infections including treatment of acne, fungal infections of the scalp, fungal or bacterial infections related to surgical or traumatic wounds, chronic or poorly healing skin lesions (especially in diabetes), vaginal infections (vaginitis), eye and ear infections, burn wounds, infections of mouth and throat, localized infections such as chronic pulmonary infections in cystic fibrosis, emphysema and asthma.

Topical infections are characterized by opportunistic colonization of a wide range of endogenous and exogenous pathogenic cells. Treatment of severe wounds such as burns or poorly healing wounds, e.g., foot ulcers in diabetes mellitus patients, require long-term administration of antibiotics, which leads to selection of resistant bacteria such as *Streptococcus pyogenes* or the methicilin-resistant *Staphylococcus aureus*. These problems could be overcome by the lipopeptides of the invention due to their wide spectrum of activity and their ability to act against non-resistant and resistant bacteria and fungi. The observed resistance of the lipopeptides to proteolytic digestion may enable them to reach the digestive system in intact form and to eliminate there bacterial infections such as chronic gastric mucosal infestation by *Helicobacter pylori* and intestinal bacterial infections.

The activity of the lipopeptides against different strains of fungi indicate their potential use for the treatment of nail fungus such as: (i) onychomycoses, the most current nail infection caused mainly by dermatophytes, in particular by *Trichophyton rubrum*, and less frequently by *Trichophyton mentagrophytes* and *Epidermophyton floccosum*; (ii) infections caused by mold; and (iii) infections caused by yeasts, particularly *Candida albicans*, as in chronic paronychia and onycholysis, and chronic mucocutaneous candidosis.

The pharmaceutical compositions can be used in the treatment of benign or malignant solid or non-solid tumors. As the lipopeptides of the invention inhibit tumor cell growth (see Example 7 herein below), the use of these conjugates can be highly advantageous in treating cancer diseases.

All types of cancers may be included in the scope of the present invention. As a non limiting example, the following cancers can be treated: skin (e.g., squamous cell carcinoma, basal cell carcinoma, or melanoma), breast, colorectal, prostate, brain and nervous system, head and neck, testicular, ovarian, pancreatic, lung, liver (e.g., hepatoma), kidney, bladder, gastrointestinal, bone, endocrine system (e.g., thyroid and pituitary tumors), and lymphatic system (e.g., Hodgkin's and non-Hodgkin's lymphomas) cancers. Cancers of the nervous system include, for example, astrocytoma, pligodendroglioma, menigioma, neuroblastoma, glioblastoma, ependyoma, Schwannoma, neurofibrosarcoma, neuroblastoma, and medullablastoma Other types of cancer include fibrosarcoma, epidermoid carcinoma, and any other cancer that form solid tumors. Also contemplated in the present invention benign proliferative diseases of the blood and malignant proliferative diseases of the blood, for example, leukemia.

Additionally, the pharmaceutical compositions of the present invention are well suited for combination with other active components intended for topical, intralesional, or any other type of application. For example, the methods of treating cancer in a subject can be carried out in conjunction with chemotherapy or radiotherapy. Thus, the pharmaceutical compositions of the invention may be administered with chemotherapeutic agents. Examples of chemotherapeutic agents that may be used include alkylating agents, antineoplastic antibiotics, antimetabolites, and a like.

It is further understood that the amount of the pharmaceutical composition administered to any particular subject will depend upon a variety of factors including, but not limited to, the type, location, and extent of the microbial infection, the extent, density, location, and type of tumor cells to be killed as well as the age, body weight, general health, and gender of the subject, and the route of administration. Administration of the pharmaceutical composition should be continued until the infection eradicated or the tumor regresses and health has been restored to the subject.

The present invention further provides methods for disinfecting an object comprising contacting an object with a microbicidally effective amount of a disinfecting composition comprising a lipophilic conjugate of the invention.

The invention will now be described with reference to some non-limiting examples.

EXAMPLES

Experimental Procedures (i) Materials

4-Methyl benzhydrylamine resin (BHA) and butyloxycarbonyl (Boc) amino acids were purchased from Calbiochem-Novabiochem Co. (La Jolla, Calif., USA). Other reagents used for peptide synthesis included trifluoroacetic acid (TFA, Sigma), N,N-diisopropylethylamine (DIEA, Sigma), dicyclohexylcarbodiimide (DCC, Fluka), 1-hydroxybenzotriazole (1-HOBT, Pierce), and dimethylformamide (DMF, peptide synthesis grade, Biolab, IL). All other reagents were of analytical grade. Buffers were prepared in double-distilled water.

(ii) Peptide Synthesis, Acylation and Purification

Peptides were synthesized by a solid phase method on 4-methyl benzhydrylamine resin (BHA) (0.05 meq) (Merrifield et. al., 1982; Shai et. al., 1990). The resin-bound peptides were cleaved from the resin by hydrogen fluoride (HF) and, after HF evaporation, and washing with dry ether, extracted with 50% acetonitrile/water. HF cleavage of the peptides bound to BHA resin resulted in C-terminus amidated peptides. Each crude peptide contained one major peak, as revealed by RP-HPLC (reverse phase high-performance liquid chromatography) that was 60-80% pure peptide by weight. The synthesized peptides were further purified by RP-HPLC on a $C_{18}$ reverse phase Bio-Rad semi-preparative column (250×10 mm, 300 nm pore size, 5-µm particle size). The column was eluted in 40 min, using a linear gradient of 25-60% acetonitrile in water, both containing 0.05% TFA (v/v), at a flow rate of 1.8 ml/min. The purified peptides, which were shown to be homogeneous (~95%) by analytical HPLC, were subjected to amino acid analysis and electrospray mass spectroscopy to confirm their composition and molecular weight. The fatty acid was conjugated to the N-terminus of the peptides using the same protocol used to attach protected amino acids for peptide synthesis.

(iii) Synthesis of the Cyclic Lipopeptides.

The cyclic peptides were synthesized by a solid-phase method as described in section (ii) above, without or with cysteine residues at both the N- and C-termini of the peptides. The cyclization without cysteine is carried out by protecting the N-terminal, activating the C-terminal, deprotecting the N-terminal, and reacting the C- and N-terminal groups while still bound to the resin. The fatty acids, in this specific case, are attached to one of the lysines. When the peptide contains cysteine residues at both the N- and C-termini, after acylation of the N-terminal or another lysine in the backbone, HF cleavage and RP-HPLC purification, the peptides are solubilized at low concentration in PBS (pH 7.3), and cyclization is completed after 12 h. The cyclic peptides are further purified on RP-HPLC and subjected to amino acid analysis to confirm their composition, and SDS-PAGE to confirm their monomeric state.

Example 1

Synthesis of 12-mer Linear Lipopeptides and Cyclic Peptides

The following lipopeptides were synthesized as described in the Experimental Procedures sections (ii) and (iii). Decanoic acid (DA), undecanoic (UA), dodecanoic acid (DDA), myristic (MA), or palmitic (PA) acid were conjugated to 12-mer C-amidated all L-amino acid or diastereomeric peptides to yield the lipophilic conjugates. The peptides contained a hydrophobic amino acid selected from Gly, Ala, Val, or Leu and the positively charged amino acid Lys. Each of the diastereomeric peptides contained 4-6 amino acid residues in the D-configuration. The lipopeptides will be designated hereinafter by numerals.

1 $[D]\text{-}K^{1,5,9,12}\text{-}K_4G_8$-MA of the sequence:
$(CH_3\text{-}(CH_2)_{12}\text{-}CO\text{-})$-D-Lys-Gly-Gly-Gly-D-Lys-Gly-Gly-Gly-D-Lys-Gly-Gly-D-Lys-$NH_2$ 2 $[D]\text{-}K^{1,5,9,12}\text{-}K_4G_8$-PA of the sequence:
$(CH_3\text{-}(CH_2)_{14}\text{-}CO\text{-})$-D-Lys-Gly-Gly-Gly-D-Lys-Gly-Gly-Gly-D-Lys-Gly-Gly-D-Lys-$NH_2$ 3 $K_4G_8$-MA of the sequence:
$(CH_3\text{-}(CH_2)_{12}\text{-}CO\text{-})$-Lys-Gly-Gly-Gly-Lys-Gly-Gly-Gly-Lys-Gly-Gly-Lys-$NH_2$ 4 $K_4G_8$-PA of the sequence:
$(CH_3\text{-}(CH_2)_{14}\text{-}CO\text{-})$-Lys-Gly-Gly-Gly-Lys-Gly-Gly-Gly-Lys-Gly-Gly-Lys-$NH_2$ 5 $[D]\text{-}A^{3,4,8,10}\text{-}K_4A_8$-PA of the sequence:
$(CH_3\text{-}(CH_2)_{14}\text{-}CO\text{-})$-Lys-Ala-D-Ala-D-Ala-Lys-Ala-Ala-D-Ala-Lys-D-Ala-Ala-Lys-$NH_2$ 6 $K_4A_8$-PA of the sequence:
$(CH_3\text{-}(CH_2)_{14}\text{-}CO\text{-})$-Lys-Ala-Ala-Ala-Lys-Ala-Ala-Ala-Lys-Ala-Ala-Lys-$NH_2$ 7 $[D]\text{-}V^{3,4,8,10}\text{-}K_4V_8$-PA of the sequence:
$(CH_3\text{-}(CH_2)_{14}\text{-}CO\text{-})$-Lys-Val-D-Val-D-Val-Lys-Val-Val-D-Val-Lys-D-Val-Val-Lys-$NH_2$ 8 $[D]\text{-}L^{3,4,8,10}\text{-}K_4L_8$-PA of the sequence:
$(CH_3\text{-}(CH_2)_{14}\text{-}CO\text{-})$-Lys-Leu-D-Leu-D-Leu-Lys-Leu-Leu-D-Leu-Lys-D-Leu-Leu-Lys-$NH_2$ 9 $[D]\text{-}L^{3,4,8,10}\text{-}K_4L_8$-MA of the sequence:
$(CH_3\text{-}(CH_2)_{12}\text{-}CO\text{-})$-Lys-Leu-D-Leu-D-Leu-Lys-Leu-Leu-D-Leu-Lys-D-Leu-Leu-Lys-$NH_2$ 10 $[D]\text{-}L^{3,4,8,10}\text{-}K_4L_8$-UA of the sequence:
$(CH_3\text{-}(CH_2)_9\text{-}CO\text{-})$-Lys-Leu-D-Leu-D-Leu-Lys-Leu-Leu-D-Leu-Lys-D-Leu-Leu-Lys-$NH_2$ 11 $[D]\text{-}L^{1,4,5,8,9,12}\text{-}L_6K_6$-DA of the sequence:
$(CH_3\text{-}(CH_2)_8\text{-}CO\text{-})$-D-Leu-Lys-Lys-D-Leu-D-Leu-Lys-Lys-D-Leu-D-Leu-Lys-Lys-D-Leu-$NH_2$ 12 $[D]\text{-}L^{1,4,5,8,9,12}\text{-}L_6K_6$-DDA of the sequence:
$(CH_3\text{-}(CH_2)_{10}\text{-}CO\text{-})$-D-Leu-Lys-Lys-D-Leu-D-Leu-Lys-Lys-D-Leu-D-Leu-Lys-Lys-D-Leu-$NH_2$ 13 $[D]\text{-}L^{1,4,5,8,9,12}\text{-}L_6K_6$-MA of the sequence:
$(CH_3\text{-}(CH_2)_{12}\text{-}CO\text{-})$-D-Leu-Lys-Lys-D-Leu-D-Leu-Lys-Lys-D-Leu-D-Leu-Lys-Lys-D-Leu-$NH_2$ 14 $[D]\text{-}L^{1,4,5,8,9,12}\text{-}L_6K_6$-PA of the sequence:
$(CH_3\text{-}(CH_2)_{14}\text{-}CO\text{-})$-D-Leu-Lys-Lys-D-Leu-D-Leu-Lys-Lys-D-Leu-D-Leu-Lys-Lys-D-Leu-$NH_2$ The following cyclic amidated lipopeptides 15 to 20 were prepared:

15 Cyclic-$[D]\text{-}A^{3,4,8,10}\text{-}K_4A_8$-PA of the sequence:

PA-Cys-Lys-Ala-D-Ala-D-Ala-Lys-Ala-Ala-D-Ala-Lys-D-Ala-Ala-Lys-Cys-$NH_2$

16 Cyclic-$[D]\text{-}K^{1,5,9,12}\text{-}K_4G_8$-MA of the sequence:

MA-Cys-D-Lys-Gly-Gly-Gly-D-Lys-Gly-Gly-Gly-D-Lys-Gly-Gly-D-Lys-Cys-$NH_2$

-continued

17 Cyclic-[D]-K$^{1,5,9,12}$-K$_4$G$_8$-PA of the sequence:

PA-Cys-D-Lys-Gly-Gly-Gly-D-Lys-Gly-Gly-Gly-D-Lys-Gly-Gly-D-Lys-Cys-NH$_2$

18 Cyclic-[D]-A$^{3,4,8,10}$-K$_4$A$_8$-MA of the sequence:

MA-Cys-Lys-Ala-D-Ala-D-Ala-Lys-Ala-Ala-D-Ala-Lys-D-Ala-Ala-Lys-Cys-NH$_2$

19 Cyclic-K$_4$G$_8$-MA of the sequence:

MA-Cys-Lys-Gly-Gly-Gly-Lys-Gly-Gly-Gly-Lys-Gly-Gly-Lys-Cys-NH$_2$

20 Cyclic-K$_4$G$_8$-PA of the sequence:

PA-Cys-Lys-Gly-Gly-Gly-Lys-Gly-Gly-Gly-Lys-Gly-Gly-Lys-Cys-NH$_2$

Additional linear lipopeptides were synthesized, the peptides contained Leu as the hydrophobic amino acid residue and Arg, His, Lys, or a combination thereof as the positively charged amino acid residues:

21 [D]-L$^{1,4,5,8,9,12}$-L$_6$K$_6$-DA of the sequence:
(CH$_3$—(CH$_2$)$_8$—CO-)-D-Leu-Lys-Lys-D-Leu-D-Leu-Lys-Lys-D-Leu-D-Leu-Lys-Lys-D-Leu-NH$_2$ 22 [D]-L$^{1,4,5,8,9,12}$-L$_6$K$_6$-DDA of the sequence:
(CH$_3$—(CH$_2$)$_{10}$—CO-)-D-Leu-Lys-Lys-D-Leu-D-Leu-Lys-Lys-D-Leu-D-Leu-Lys-Lys-D-Leu-NH$_2$ 23 [D]-L$^{1,4,5,8,9,12}$-L$_6$K$_6$-MA of the sequence:
(CH$_3$—(CH$_2$)$_{12}$—CO-)-D-Leu-Lys-Lys-D-Leu-D-Leu-Lys-Lys-D-Leu-D-Leu-Lys-Lys-D-Leu-NH$_2$ 24 [D]-L$^{1,4,5,8,9,12}$-L$_6$K$_6$-PA of the sequence:
(CH$_3$—(CH$_2$)$_{14}$—CO-)-D-Leu-Lys-Lys-D-Leu-D-Leu-Lys-Lys-D-Leu-D-Leu-Lys-Lys-D-Leu-NH$_2$ 25 [D]-L$^{1,4,5,8,9,12}$-L$_6$R$_6$-DDA of the sequence:
(CH$_3$—(CH$_2$)$_{10}$—CO-)-D-Leu-Arg-Arg-D-Leu-D-Leu-Arg-Arg-D-Leu-D-Leu-Arg-Arg-D-Leu-NH$_2$ 26 [D]-L$^{1,4,5,8,9,12}$-L$_6$H$_6$-DDA of the sequence:
(CH$_3$—(CH$_2$)$_{10}$—CO-)-D-Leu-His-His-D-Leu-D-Leu-His-His-D-Leu-D-Leu-His-His-D-Leu-NH$_2$ 27 [D]-L$^{1,4,5,8,9,12}$-L$_6$R$_3$H$_3$-DDA of the sequence:
(CH$_3$—(CH$_2$)$_{10}$—CO-)-D-Leu-Arg-His-D-Leu-D-Leu-Arg-His-D-Leu-D-Leu-Arg-His-D-Leu-NH$_2$ 28 [D]-L$^{1,4,5,8,9,12}$-L$_6$K$_3$H$_3$-DDA of the sequence:
(CH$_3$—(CH$_2$)$_{10}$—CO-)-D-Leu-Lys-His-D-Leu-D-Leu-Lys-His-D-Leu-D-Leu-Lys-His-D-Leu-NH$_2$ Example 2

Mass Spectrometry and Retention Time of the Lipopeptides

The lipopeptides were subjected to C$_4$ RP-HPLC to determine the effect of the fatty acid on the retention time of the lipophilic conjugates.

The amidated lipopeptides were applied on an analytical C$_4$ column and eluted within 80 min using a linear gradient of 0 to 80% acetonitrile in water containing 0.05% TFA (v/v). The molecular weight of the lipopeptides was obtained by mass spectrometry.

TABLE 1

Sequence, molecular weight, and retention time of the lipopeptides.

| Conjugate Designation | Sequence | Calculated Molecular Weight (gr/mole) | RP-HPLC Retention Time (minutes) |
|---|---|---|---|
| [D]-L$_6$K$_6$ | L KK L L K K L L K K L -NH$_2$ | 1466 | 16.3 |
| [D]-L$_6$K$_6$-DA - 21 | CH$_3$(CH$_2$)$_8$CO-L KK L L K K L L K K L -NH$_2$ | 1620.3 | 29.9 |
| [D]-L$_6$K$_6$-DDA - 22 | CH$_3$(CH$_2$)$_{10}$CO-L KK L L K K L L K K L -NH$_2$ | 1648.3 | 32.9 |
| [D]-L$_6$K$_6$-MA-23 | CH$_3$(CH$_2$)$_{12}$CO-L KK L L K K L L K K L -NH$_2$ | 1676.3 | 36.1 |
| [D]-L$_6$K$_6$-PA- 24 | CH$_3$(CH$_2$)$_{14}$CO-L KK L L K K L L K K L -NH$_2$ | 1704.3 | 41.5 |

Note:
The D-amino acid residues are denoted by bold letters and underline.

Table 1 shows that as the length of the aliphatic chain of the fatty acid increases, the retention time as well as the molecular weight of the lipophilic conjugate increase.

TABLE 2

Sequence and retention time of the lipopeptides.

| Conjugate Designation | Sequence | RP-HPLC Retention Time (minutes) |
|---|---|---|
| DL6R6 | LRRLLRRLLRRL | 15.5 |
| DDA-DL6R6 - 25 | DDA- LRRLLRRLLRRL | 25.7 |
| DL6H6 | LHHLLHHLLHHL | 16 |
| DDA-DL6H6 - 26 | DDA-LHHLLHHLLHHL | 28 |
| DL6R3H3 | LRHLLRHLLRHL | 18.6 |
| DDA-DL6R3H3 - 27 | DDA-LRHLLRHLLRHL | 27 |
| DL6K6 | LKKLLKKLLKKL | 14.3 |
| DDA-DL6K6 - 22 | DDA-LKKLLKKLLKKL | 24.3 |
| DL6K3H3 | LKHLLKHLLKHL | 15.5 |
| DDA- DL6K3H3 - 28 | DDA- LKHLLKHLLKHL | 26 |

Table 2 shows that as the length of the aliphatic chain of the fatty acid increases, the retention time of the lipophilic conjugate increases.

Example 3

Antibacterial Activity of the Lipopeptides at pH 7.4 and pH 5.5

The antibacterial activity of the lipopeptides was examined in sterile 96-well plates (Nunc F96 microtiter plates) in a final volume of 100 µl as follows: Aliquots (50 µl) of a suspension containing bacteria at concentration of $1 \times 10^6$ Colony-Forming Units (CFU)/ml in culture LB (Lauria broth) medium (pH 7.4 or pH 5.5) were added to 50 µl of water containing the lipopeptide in serial 2-fold dilutions in water. Adjustment of the pH was done by diluted solutions of HCl and NaOH. Inhibition of growth was determined by measuring the absorbance at 600 nm with a Microplate autoreader E1309 (Bio-Tek Instruments), after an incubation time of 18-20 h at 37° C. Antibacterial activities were expressed as the minimal inhibitory concentration (MIC), the concentration at which 100% inhibition of growth was observed after 18-20 h of incubation. The bacteria used were: *Escherichia coli* ATCC 25922, *Acinetobacter baumannii* ATCC 19606, *Pseudomonas aeruginosa* ATCC 27853, *Staphylococcus aureus* ATCC 6538P, *Enterococcus faecalis* ATCC 29212, *Enterobacter cloacae* ATCC 49141. The antibacterial activity of lipopeptides was also examined against resistant bacteria: methicilin-resistant *Staphylococcus aureus* (MRSA) ATCC 700698 and vancomycin-resistant *Enterococcus faecium* (VRE) ATCC 700221. If not indicated otherwise, the bacterial growth was detected at pH 7.4.

TABLE 3

Minimal Inhibitory Concentration (µM) of short lipopeptides on bacteria growth.

| Conjugate | S. aureus ATCC 6538P | A. baumannii ATCC 19606 | E. coli-D21 | P. aeruginosa ATCC 27853 | M. laleus |
|---|---|---|---|---|---|
| PA-KKKK | 25 | nd | 12.5 | 3.12 | 3.12 |
| PA-KGGK | 50 | nd | 25 | 12.5 | 3.12 |
| PA-KLLK | 3.12 | nd | 100 | 100 | 3.12 |
| PA-KAAK | 6.25 | 100 | 6.25 | 100 | nd |
| PA-K | >100 | >100 | >100 | >100 | nd |
| PA-KK | 6.25 | 100 | 6.25 | 100 | 3.12 |
| PA-KKK | 12.5 | 12.5 | 6.25 | 50 | 3.12 |
| PA-KKK | 6.25 | 12.5 | 6.25 | 25 | nd |
| MYR-KKK | 12.5 | >100 | 25 | | nd |
| PA-EKKK | 12.5 | >100 | 25 | >100 | nd |
| PA-RLLR | 25 | >100 | >100 | >100 | nd |
| PA-KE | >100 | >100 | >100 | >100 | nd |
| PA-EKE | 25 | >100 | 100 | >100 | nd |
| PA-KKEK | 25 | 100 | 25 | 100 | nd |
| Gentamycin | 6.25 | 3.12 | 1.56 | 0.78 | 0.78 | nd—not determined

As shown in Table 3, lipopeptides, which contain either short peptides of all L-amino acid residues or short diastereomeric peptides, all having a positive charge that is greater than +1, exhibit antibacterial activity;

TABLE 4

Minimal Inhibitory Concentration (μM) of the lipopeptides on bacteria growth.

| Conjugate Designation | E. coli | P. Aeruginosa | A. Baumaannii | E. cloacae | E. faecalis | S. aureus | S. aureus (MRSA) | E. faecium (VRE) |
|---|---|---|---|---|---|---|---|---|
| 1 | 12.5 | 6.25 | N.D. | 3.125 | 3.125 | 6.25 | 6.25 | N.D. |
| 2 | 25 | 6.25 | 25 | 25 | 12.5 | 12.5 | 12.5 | 3.125 |
| 3 | 6.25 | 6.25 | 12.5 | 6.25 | 6.25 | 6.25 | 6.25 | 12.5 |
| 4 | 25 | 6.25 | 25 | 50 | 12.5 | 12.5 | 12.5 | N.D. |
| 5 | 6.25 | 6.25 | 6.25 | 25 | 12.5 | 12.5 | 12.5 | N.D. |
| 6 | 50 | 25 | 25 | 100 | 50 | 50 | N.D. | N.D. |
| 10 | 6.25 | 3.25 | 3.125 | 1.56 | 3.125 | 3.125 | 3.125 | N.D. |

N.D. = Not determined

The results for lipopeptides 1-6, and 10, summarized in Table 4, reveal that the lipopeptides of the invention are potent against most bacteria examined. In addition, lipopeptides 2 and 10 are highly active against VRE and MRSA, respectively, indicating that these bacteria are not resistant to the lipopeptides.

TABLE 5

Minimal Inhibitory Concentration (MIC) of the lipopeptides on bacteria growth.

| | Minimal Inhibitory Concentration (μM) Bacteria | | | |
|---|---|---|---|---|
| | Gram (+) | | Gram (−) | |
| Conjugate Designation | S. aureus ATCC 6538P | E. aerogenes ATCC 35029 | P. aeruginosa ATCC 27853 | E. coli ATCC 35218 |
| [D]-$L_6K_6$ | >50 | >50 | >50 | 50 |
| [D]-$L_6K_6$-DA | 6.25 | 50 | 12.5 | 12.5 |
| [D]-$L_6K_6$-DDA | 12.5 | 50 | 25 | 25 |
| [D]-$L_6K_6$-MA | 50 | >50 | 50 | 50 |
| [D]-$L_6K_6$-PA | 50 | >50 | >50 | 50 |

Results are the mean of 3 independent experiments, each performed in duplicate.

As shown in Table 5, fatty acids such as DA or DDA improved significantly the antibacterial activity of the diastereomeric peptide [D]-$L_6K_6$. Longer fatty acids such as MA or PA improved it slightly.

TABLE 6

Minimal inhibitory concentrations (μM) of the lipopeptides on bacteria

| Conjugate Designation | E. Coli ATCC 25922 | E. Coli D21 | P. Aeruginosa ATCC 27853 | A. baumannii ATCC 19606 | S. aureus II ATCC 6538P |
|---|---|---|---|---|---|
| DDA-DL6R6-25 | >100 | 50 | 50 | >100 | 12.5 |
| DDA-DL6H6-26 | >100 | >100 | >100 | 100 | 100 |
| DDA-DL6R3H3-27 | 100 | 100 | 100 | 100 | 100 |
| DDA-DL6K6-22 | 75 | 25 | 25 | 25 | 3.125 |
| DDA-DL6K3H3-28 | 100 | 50 | 50 | 50 | 18.75 |
| Gentamycin | 6.25 | 12.5 | 12.5 | 12.5 | 12.5 |

TABLE 7

Minimal inhibitory concentrations of the lipopeptides (μM) on bacteria growth at pH 5.5

| Conjugate Designation | E. Coli ATCC 25922 | E. Coli D21 | P. Aeruginosa ATCC 27853 | A. baumannii ATCC 19606 | S. aureus II ATCC 6538P |
|---|---|---|---|---|---|
| DDA-DL6R6 - 25 | 100 | 50 | 50 | 75 | 50 |
| DDA-DL6H6 - 26 | >100 | 100 | 100 | >100 | >100 |
| DDA-DL6R3H3-27 | 100 | 100 | 100 | >100 | 100 |

TABLE 7-continued

Minimal inhibitory concentrations of the lipopeptides (μM) on bacteria growth at pH 5.5

| Conjugate Designation | E. Coli ATCC 25922 | E. Coli D21 | P. Aeruginosa ATCC 27853 | A. baumannii ATCC 19606 | S. aureus II ATCC 6538P |
|---|---|---|---|---|---|
| DDA-DL6K6- 22 | 50 | 25 | 12.5 | 25 | >100 |
| DDA-DL6K3H3- 28 | >100 | >100 | >100 | >100 | >100 |
| Gentamycin | 12.5 | 12.5 | 12.5 | 12.5 | 25 |

As shown in Tables 6 and 7, the antibacterial activity exerted by the lipopeptides is dependent on the pH.

In order to evaluate the contribution of the fatty acids to the antibacterial activity of the lipopeptides of the invention, the antibacterial activity of the lipopeptides was compared to that of the parent peptides (without the conjugated fatty acid).

TABLE 8

Minimal Inhibitory Concentration (μM) of the lipopeptides on bacteria growth.

| | Minimal Inhibitory Concentration (μM) Bacteria | | | | |
|---|---|---|---|---|---|
| | Gram (+) | | Gram (−) | | |
| Conjugate Designation | S. aureus (ATCC 6538P) | B. subtilis (ATCC 6051) | P. aeruginosa (ATCC 27853) | A. baumannii (ATCC 19606) | E. coli (ATCC 25922) |
| DK4G8 | >100 | >100 | >100 | >100 | >100 |
| PA-DK4G8- 2 | 12.5 | 3.125 | 6.25 | 25 | 25 |
| DK4A8 | >100 | >100 | >100 | >100 | >100 |
| PA-DK4A8-5 | 12.5 | 3.125 | 6.25 | 6.25 | 6.25 |
| DK4V8 | >100 | 60 | >100 | >100 | >100 |
| PA-DK4V8-7 | >100 | >100 | >100 | >100 | >100 |

As shown in Table 8, conjugation of palmitic acid to peptides 2 and 5 was associated with significantly enhanced antibacterial activity.

Example 4

Antifungal Activity of the Lipopeptides at pH 7.4 and pH 5.5

The antifungal activity of the lipopeptides was examined in sterile 96-well plates (Nunc F96 microtiter plates) in a final volume of 200 μL as follows: 100 μl of a suspension containing fungi at a concentration of $1 \times 10^4$ Colony-Forming Units (CFU)/ml in culture medium (RPMI 1640, 0.165 M MOPS with L-glutamine, without NaHCO$_3$) at pH 7.4 or pH 5.5 (adjustment of the pH was done by diluted solutions of HCl and NaOH) were added to 100 μl of water containing the peptide in serial 2-fold dilutions in water. The fungi were incubated in the presence of the lipopeptides for 24-48 h at 35° C. in a Binder KB115 incubator under agitation. Growth inhibition was determined by measuring the absorbance at 620 nm with a Microplate autoreader E1309 (Bio-Tek Instruments). Antifungal activity is expressed as the minimal inhibitory concentration (MIC), the concentration at which 100% inhibition of fungi growth was observed after the incubation time mentioned above. The fungi used were: *Aspergillus niger* ATCC 9642, *Candida albicans* ATCC 10231 and *Cryptococcus neoformans* ATCC 66031. If not indicated otherwise, the fungi growth was detected at pH 7.4.

TABLE 9

Minimal Inhibitory Concentration (μM) of short lipopeptides on fungi growth.

| | Minimal Inhibitory Concentration (μM) | | |
|---|---|---|---|
| | Yeast | Fungi | |
| Conjugate | Candida Albicans (ATCC 10231) | Cyrptococcus neoformans (ATCC MYA-422) | Aspergillus Fomigatus (ATCC 26430) |
| PA-KKKK | 25 | 1.56 | 12.5 |
| PA-KGGK | 12.5 | 1.56 | 6.25 |
| PA-KLLK | 6.25 | 1.56 | 3.125 |
| PA-KAAK | 25 | 3.12 | 12.5 |
| PA- K | >100 | 6.25 | >100 |
| PA-KK | 12.5 | 2.5 | 6.25 |
| PA-KKK | 25 | 3.12 | 12.5 |
| PA-KKK | 25 | 3.12 | 12.5 |
| MYR-KKK | >100 | 12.5 | 100 |
| PA-EKKK | 25 | 6.25 | 12.5 |
| PA-RLLR | 25 | 1.56 | 6.25 |
| PA-KE | >100 | >100 | >100 |
| PA-EKK | 25 | 12.5 | 25 |
| PA-KKEK | 50 | 12.5 | 50 |
| Amphotericin | 0.625 | 0.312 | 1.25 |

Results are the mean of 3 independent experiments each performed in duplicates, with standard deviation of 25%.

As shown in Table 9, lipopeptides, which contain all L-amino acid short peptides or short diastereomeric peptides having a positive charge that is equal or greater than +1, exhibit antifungal activity.

TABLE 10

Minimal Inhibitory Concentration (μM) of lipopeptides on fungi growth.

| Conjugate Designation | C. albicans ATCC 10231 | C. neoformans ATCC 66031 | A. fumigatus ATCC 26430 |
|---|---|---|---|
| 1 | 3.125 | 6.25 | 6.25 |
| 2 | 3.125 | 6.25 | 12.5 |
| 3 | 3.125 | 3.125 | 6.25 |
| 4 | 3.125 | 1.56 | 6.25 |
| 5 | 12.5 | 1.56 | 100 |
| 6 | 3.125 | 1.56 | 12.5 |
| 10 | 3.125 | 1.56 | 6.25 |

The results for peptides 1-6 and 10 summarized in Table 10 show that all the lipopeptides are highly active against all the fungi examined.

TABLE 11

Minimal Inhibitory Concentration (MIC) of the lipopeptides on fungi growth.

| | Minimal Inhibitory Concentration (μM) | | |
|---|---|---|---|
| | Yeast | | Mould |
| Peptide Designation | C. albicans ATCC 10231 | C. neoformans ATCC MYA-422 | A. fumigatus ATCC 26430 |
| [D]-$L_6K_6$ | >50 | >50 | >50 |
| [D]-$L_6K_6$-DA | 25 | 1.56 | 12.5 |
| [D]-$L_6K_6$-DDA | 12.5 | 0.78 | 6.25 |
| [D]-$L_6K_6$-MA | 1.56 | 0.78 | 1.56 |
| [D]-$L_6K_6$-PA | 1.56 | 0.78 | 1.56 |

Results are the mean of 3 independent experiments, each performed in duplicates.

As shown in Table 11, conjugation of fatty acids having different length of aliphatic chain improved the antifungal activity of the diastereomeric peptide [D]-$L_6K_6$. The improvement of the antifungal activity was more significant when the peptide was conjugated to fatty acid having longer aliphatic chain such as MA or PA.

TABLE 12

Minimal inhibitory concentrations of the lipopeptides (μM) on fungi growth.

| Conjugate Designation | C. Neofor. Without serum | A. Fumig. Without serum | C. Albicans Without serum | C. Neofor. With serum | A. Fumig. With serum | C. Albicans With serum |
|---|---|---|---|---|---|---|
| DDA-DL6H6- 26 | 12.5 | >100 | >100 | 100 | 100 | >100 |
| DDA-DL6R3H3- 27 | 3.125 | 25 | 12.5 | 25 | 100 | >100 |
| DDA-DL6K3H3- 28 | 1.56 | 25 | 12.5 | 6.25 | 100 | >100 |
| DDA-DL6R6- 25 | <0.78 | 3.125 | 3.125 | <0.78 | 50 | 100 |
| DDA-DL6K6- 22 | <0.78 | 12.5 | 3.125 | <0.78 | 50 | 100 |
| Amphoterycin B | <0.78 | 2.34 | 3.125 | <0.78 | <0.78 | 0.78 |

TABLE 13

Minimal inhibitory concentrations of the lipopeptides (μM) on fungi growth at pH 5.5.

| Conjugate Designation | C. Neofor. Without serum | A. Fumig. Without serum | C. Albicans Without serum | C. Neofor. With serum | A. Fumig. With serum | C. Albicans With serum |
|---|---|---|---|---|---|---|
| DDA-DL6H6 - 26 | 3.125 | 6.25 | 9.375 | 50 | 100 | >100 |
| DDA-DL6R3H3 - 27 | 1.56 | 6.25 | 25 | 25 | 100 | >100 |
| DDA-DL6K3H3- 28 | <0.78 | 12.5 | 12.5 | 12.5 | 100 | >100 |
| DDA-DL6R6- 25 | <0.78 | 6.25 | 12.5 | 2.34 | 50 | 100 |
| DDA-DL6K6- 22 | <0.78 | 75 | 100 | 1.56 | 100 | >100 |
| Amphoterycin B | 3.125 | 3.125 | 9.375 | <0.78 | <0.78 | 0.78 |

In order to evaluate the contribution of the fatty acid to the antifungal activity of the lipopeptides of the invention, the antifungal activity of the lipopeptides was compared to that of the parent peptides.

TABLE 14

Minimal Inhibitory Concentration (µM) of the lipopeptides on fungi growth.

| | Minimal Inhibitory Concentration (µM) | | | | |
|---|---|---|---|---|---|
| | Yeast | | Fungi | | |
| Conjugate Designation | Candida albicans (ATCC 10231) | Cryptococcus neoformans (ATCC MYA-422) | Aspergillus fumigatus (ATCC 26430) | Aspergillus flavus (ATCC 9643) | Aspergillus niger (ATCC 9642) |
| DK4G8 | >100 | >100 | >100 | >100 | >100 |
| PA-DK4G8-2 | 3.125 | 6.25 | 12.5 | 100 | 6.25 |
| DK4A8 | >100 | >100 | >100 | >100 | >100 |
| PA-DK4A8-5 | 12.5 | 1.56 | 100 | 80 | 10 |
| DK4V8 | >100 | 50 | >100 | >100 | >100 |
| PA-DK4V8-7 | 3.125 | 3.125 | >100 | >100 | >100 |

As shown in Table 14, the lipopeptides listed exert enhanced antifungal activity compared to that of the parent peptides.

Thus, the group of 12-mer lipopeptides shown herein was significantly more active against bacteria and fungi than their parent peptides, which are not conjugated to fatty acids.

Example 5

Hemolytic Activity of the Lipopeptides

The effect of the lipopeptides of the invention on red blood cell hemolysis was next tested.

Fresh human red blood cells (hRBC) with EDTA were rinsed 3 times with PBS (35 mM phosphate buffer/0.15 M NaCl, pH 7.3) by centrifugation for 10 min at 800 g and resuspended in PBS. Peptides dissolved in PBS were then added to 50 µL of a solution of the stock hRBC in PBS to reach a final volume of 100 µL (final erythrocyte concentration, 4% v/v). The resulting suspension was incubated under agitation for 60 min at 37° C. The samples were then centrifuged at 800×g for 10 min. Release of hemoglobin was monitored by measuring the absorbance of the supernatant at 540 nm. Controls for zero hemolysis (blank) and 100% hemolysis consisted of hRBC suspended in PBS and Triton 1%, respectively.

Figure 6:
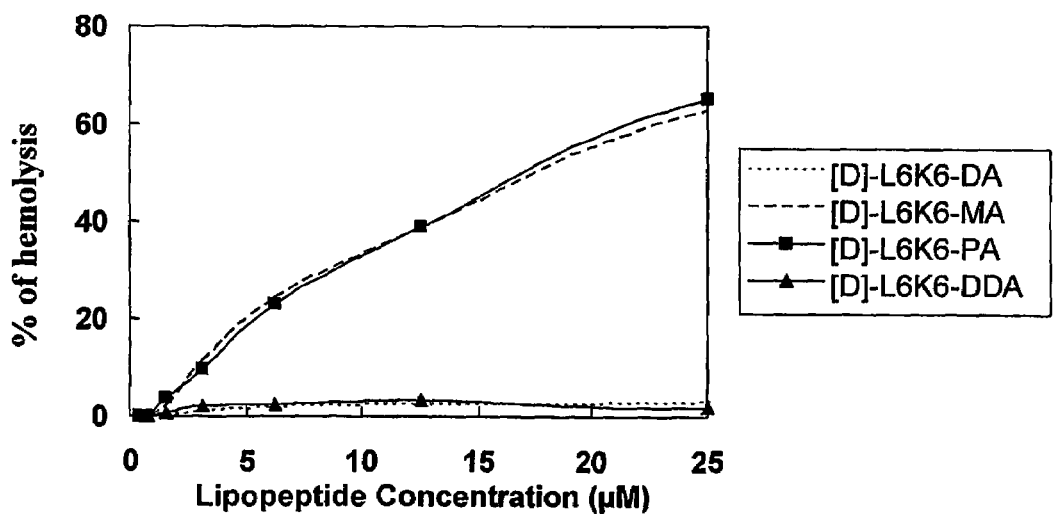
FIG. 6 shows the effect of different fatty acids on the hemolytic activity of lipopeptides. A 12-mer diastereomeric peptide was coupled either to decanoic acid, dodecanoic acid, myristic acid or to palmitic acid and the hemolytic activity of the conjugates was monitored by measuring the absorbance at 540 nm.
Figure 7A:
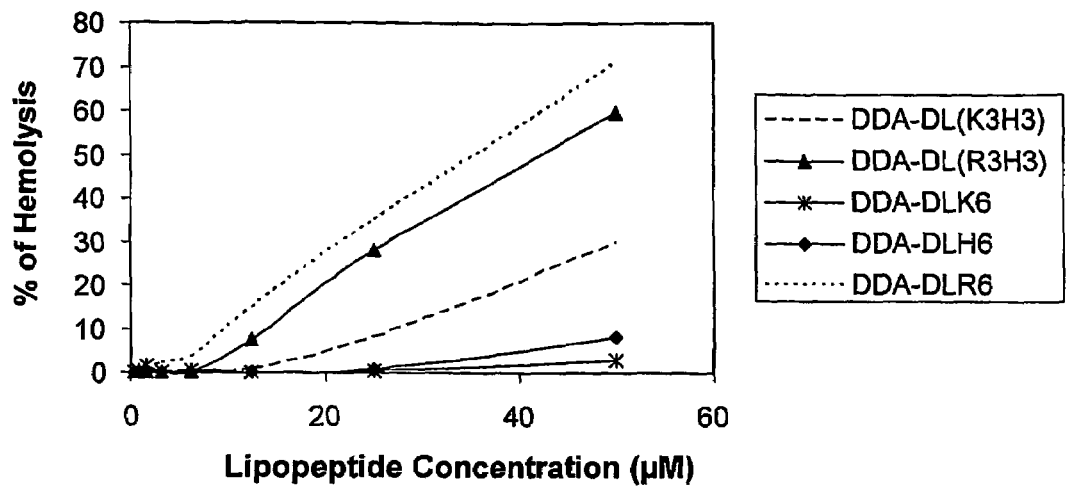
FIGS. 7A-B show the hemolytic activity of lipopeptides having the same fatty acid, but varying in the peptide moiety. Dodecanoic acid was coupled to 12-mer peptides, which are composed of six Leu residues and six positively charged amino acid residues of either Lys, His, Arg, or a combination thereof. The hemolytic activity of the lipopeptides was determined at neutral pH (FIG. 7A) or at acidic pH (FIG. 7B) by measuring the absorbance at 540 nm.
Figure 7B:
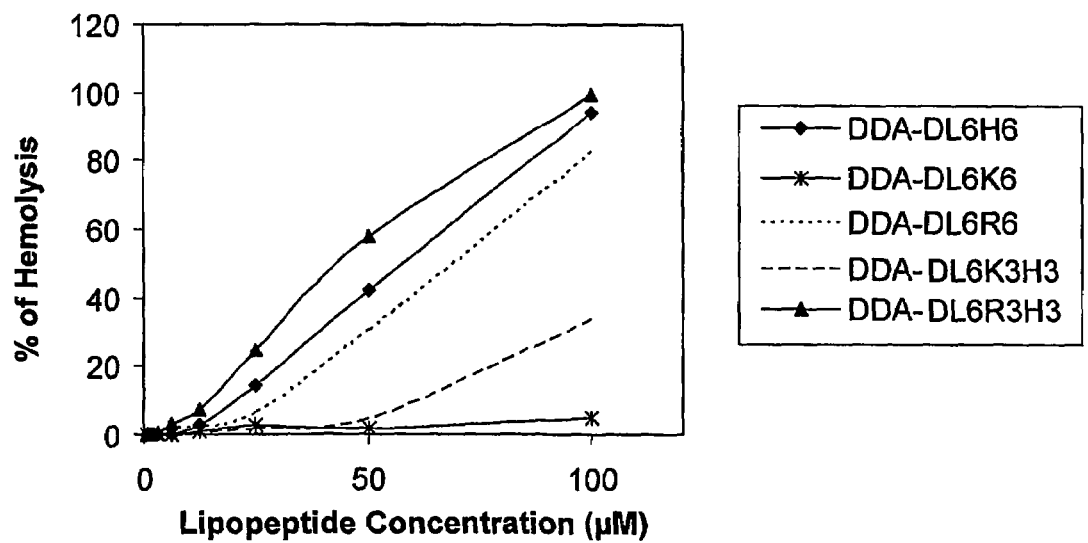

FIGS. 1-7 show the hemolytic effect of the lipopeptides of the invention. Short lipopeptides containing 1 to 4 amino acid residues (FIGS. 1-4) and the 12-mer lipopeptides 2, 4, 5 and 6 (FIG. 5) do not exhibit significant hemolytic activity at concentrations lower than 12 µM, at which concentrations that they exert specific antifungal and antibacterial activities. Similarly, lipopeptides 22, 26, and 28 do not exert hemolytic activity up to a concentration of 25 µM (FIGS. 6-7).

Example 6

Resistance of the Lipopeptides to Proteolytic Digestion

In order to reach their target, the lipopeptides have to withstand proteolytic digestion by proteases. Such degradation may occur from the time the lipopeptides have been administered at one site till they reach their target site.

Equal amounts of the lipopeptides were dissolved in PBS (35 mM phosphate buffer/0.15 M NaCl, pH 7.3) to yield a final concentration of 140 µM to which 25 µM of either pepsin (from porcine stomach mucosa, Sigma), trypsin (from bovine pancreas, Sigma), or elastase (from human leukocytes, Sigma) were added. The samples were incubated under agitation for 30 min at 37° C. After addition of the appropriate protease inhibitor to stop the reaction, aliquots of the proteolytic digest were injected to $C_{18}$ HPLC column and the amounts of the intact lipopeptide were evaluated using their absorbance at 215 nm.

TABLE 15

| Proteolytic digestion (%) of the diastereomers. | | | |
|---|---|---|---|
| Conjugate Designation | Trypsin | Pepsin | Elastase |
| 16 | 0 | 0 | 0 |
| 19 | 100 | 100 | 100 |

The results summarized in Table 15 show that lipopeptide 16 of the invention is protected from proteolytic digestion by pepsin, trypsin, and elastase as assessed by reverse-phase HPLC. As a control, lipopeptide 19, which contains all L-amino acid residues with the same sequence as that of lipopeptide 16, was used. Thus, introducing D-amino acids within the sequence of a particular lipopeptide significantly protects it from enzymatic degradation.

Example 7

The Anticancer Activity of the Lipopeptides

Prostate cancer cell lines (CL1 and 22RV1; ATCC, USA) were grown in RPMI-1640 supplemented with 10% FCS (Biological Industries, Beit Haemek, Israel). NIH-3T3 mouse fibroblast cell line (ATCC, USA) was grown in DMEM supplemented with 10% bovine serum. To test cytotoxicity against the cancer cells, aliquots of medium containing $1 \times 10^4$ cells were distributed into a 96-well plate (Falcon). After one day, the media were replaced with 90 µl of fresh media and 10 µl of a solution containing different concentrations of the peptides. The plate was then incubated for 24 h before adding to each well 50 µl of XTT reaction solution (Biological Industries, Beit Haemek, Israel); viability was determined as previously described (Papo et al., (2003) J. Biol. Chem. 278: 21018-23). The LC50 (concentration at which 50% of the cells die) for each peptide was obtained from the dose-dependent cell viability curves.

TABLE 16

LC50 of the lipopeptides (μM) against prostate cancer and non-cancer cell lines.

| Conjugate Designation | Prostate cancer 22RV1 | Prostate cancer CL1 | 3T3 |
|---|---|---|---|
| DL6K6 | >100 | >100 | >100 |
| DDA-DL6K6 - 22 | <3.125 | <3.125 | 50 |
| MA-DL6K6 - 23 | <3.125 | <3.125 | 50 |
| PA-DL6K6 - 24 | <3.125 | 3.125 | 50 |
| DL6R6 | 50 | >100 | >100 |
| DDA-DL6R6 - 25 | 3.125 | 3.125 | 100 |

As shown in Table 16, coupling of a fatty acid to the diastereomeric peptides [D]L$_6$K$_6$ or [D]-L$_6$R$_6$ improved significantly the cytotoxic effect of the lipopeptides against cancer cells with almost no effect on normal cells.

In Vivo Studies with PC Xenografts

Subcutaneously (s.c.) implantation of human PC in mice is done as described by Gavish Z, et al. (Prostate 2002; 51:73-83). Briefly, 0.1 ml AI CL1 and 22RV1 human PC cells (5×10$^6$ cells) in Matrigel (Biological Industries, Beit Haemek, Israel) is inoculated s.c. into the dorsal side of five to six week-old nude male mice weighing 20-25 g (Harlen Co., Israel). Two weeks after cell implantation, when the tumor diameter reaches ≧5 mm (this day is denoted day 1), the all L-amino acid peptide and its diastereomeric peptide (at 1 mg/kg, 0.1 mM), or vehicle (PBS, pH=7.4) are injected intratumorally (dosing volume of 2.5 ml/kg) three times a week for a total of 9 doses. Tumor size is measured by a caliper and recorded twice a week during a period of 28 days. Mice are weighed and tumor weight (mg) is estimated by using the formula of length×width×depth×0.52 in mm$^3$, assuming the specific gravity to be 1. At the end of the treatment, the mice are killed, and the tumors are removed, photographed, and weighed. The animal experimentation are reviewed and approved by the Institutional Animal Care and Use Committee.

Example 8

Antimicrobial Activity of Diastereomeric Magainin Conjugated to a Fatty Acid

Previous studies indicated that coupling of a fatty acid to an antibacterial peptide, a magainin analog, resulted in endowing the peptide with antifungal activity (18). It should be noted that the peptide was devoid of antifungal activity before its coupling to the fatty acid.

In order to evaluate whether conjugation of a fatty acid to a diastereomeric magainin analog can endow the peptide with antifungal activity, the magainin analog was synthesized as to contain four D-amino acid residues. The sequence of the diastereomeric magainin analog is as follows:

Gly-Ile-Gly-Lys-Phe-D-Leu-His-Ser-Ala-D-Lys-Lys-Trp-Gly-Lys-Ala-D-Phe-Val-Gly-D-Glu-Ile-Met-Asn-Ser-NH$_2$.

To the parent diastereomeric magainin analog, various fatty acids were conjugated.

TABLE 17

Minimal Inhibitory Concentration (mM) of D-magainin analog on fungi and yeast growth.

| | Minimal Inhibitory Concentration (μM) | | | |
|---|---|---|---|---|
| | Yeast | | Fungi | % of |
| Peptide Designation | Candida albicans (ATCC 10231) | Cyrptococcus neoformans (ATCC MYA-422) | Aspergillus fumigatus (ATCC 26430) | Hemolytic activity at maximal MIC |
| [D]4magainin | >50 | >50 | >50 | — |
| [D]4magainin-UA | >50 | 6.25 | >50 | 2% |
| [D]4magainin-PA | >50 | 6.25 | >50 | 8% |

Results are the mean of 3 independent experiments each performed in duplicates, with standard deviation of 25%.

TABLE 18

Minimal Inhibitory Concentration (mM) of D-magainin analog on bacteria growth.

| | Minimal Inhibitory Concentration (μM) | | | |
|---|---|---|---|---|
| | Gram Negative | | Gram Positive | |
| Peptide Designation | E. coli ATCC 25922 | P. aeruginosa ATCC 27853 | B. subtilis ATCC 6051 | S. aureus ATCC 6538P |
| [D]4magainin | >50 | >50 | 50 | >50 |
| [D]4magainin-UA | >50 | 50 | 6.25 | 50 |
| [D]4magainin-PA | >50 | >50 | 50 | >50 |

Results are the mean of 3 independent experiments each performed in duplicates, with standard deviation of 25%.

The results in Tables 17 and 18 show that [D]-magainin is practically not active toward fungi and bacteria. Attachment of a fatty acid to the inactive [D]-magainin improved slightly its antibacterial activity i.e., only against *B. subtilis*, and endowed it with antifungal activity only against *C. neoformans* (Tables 17 and 18). As the secondary structure of [D]-magainin was preserved compared to the secondary structure of the parent peptide, and as the conjugation of the fatty acids did not affect [D]-magainin structure, these results indicate that conjugation of a fatty acid to a peptide having high hydrophobicity of its own cannot always "rescue" an inactive peptide.

It will be appreciated by persons skilled in the art that the present invention is not limited by what has been particularly shown and described herein above. Rather the scope of the invention is defined by the claims that follow.

The invention claimed is:

1. A lipophilic conjugate comprising a peptide coupled to a fatty acid, the peptide or a salt thereof consisting of 2 to 14 amino acid residues having a net positive charge that is equal or greater than +1 comprising at least two positively charged amino acid residues, said peptide after conjugation to the fatty acid having at least one activity selected from the group consisting of antibacterial, antifungal, and anticancer activity, wherein the activity after conjugation being higher than prior to conjugation, the peptide prior to conjugation of said fatty acid being devoid of or having very weak antibacterial and antifungal activity, wherein the lipophilic conjugate is selected from the group of lipopeptides set forth in SEQ ID NOS: 1 to 38.

2. A method for treating a bacterial or fungal infection in a subject comprising administering to a subject in need thereof a therapeutically effective amount of a pharmaceutical composition comprising a carrier and, as an active ingredient, a lipophilic conjugate according to claim 1.

3. The method according to claim 2, wherein administering the pharmaceutical composition to the subject is selected from topical, intravenous, intraarterial, intramuscular, intraperitoneal, oral, ophthalmic, nasal, vaginal, rectal, and intralesional administration.

4. The method according to claim 3, wherein administering the pharmaceutical composition is by topical administration.

5. The method according to claim 2, wherein the infection is a bacterial infection.

6. The method according to claim 5, wherein the bacterial infection is caused by antibiotic-resistant bacteria.

7. The method according to claim 6, wherein the antibiotic-resistant bacteria are selected from *Streptococcus pyogenes* and *Staphylococcus aureus*.

8. The method according to claim 2, wherein the infection is a fungal infection.

9. The method according to claim 2, wherein the subject has acne, poorly healing skin lesions, or burn wounds or the infection is selected from fungal infections of the scalp, fungal infections related to traumatic wounds, bacterial infections related to traumatic wounds, and bacterial or fungal eye or ear infections.

10. A method for treating prostate cancer in a subject comprising administering to a subject in need thereof a therapeutically effective amount of a pharmaceutical composition comprising as an active ingredient a lipophilic conjugate according to claim 1.

11. The method according to claim 10, wherein the administering of the pharmaceutical composition is into the prostate or adjacent to the prostate.

12. A method for reducing bacterial or fungal growth on an object comprising contacting the object with a composition comprising as an active ingredient a lipophilic conjugate according to claim 1.

13. The method according to claim 12, wherein the object is selected from the group consisting of tissue culture equipment, tissue culture media, tissue culture incubators, tissue culture hoods, and tissue culture dishes.

14. The method according to claim 12, wherein the object is selected from medical and surgical equipment.

* * * * *

UNITED STATES PATENT AND TRADEMARK OFFICE
CERTIFICATE OF CORRECTION

| | | |
|---|---|---|
| PATENT NO. | : 7,671,011 B2 | Page 1 of 1 |
| APPLICATION NO. | : 10/560727 | |
| DATED | : March 2, 2010 | |
| INVENTOR(S) | : Shai et al. | |

It is certified that error appears in the above-identified patent and that said Letters Patent is hereby corrected as shown below:

Title Page:
Item (57) ABSTRACT, line 2, change "acid The" to -- acid. The --.

Signed and Sealed this

Thirteenth Day of July, 2010

David J. Kappos
*Director of the United States Patent and Trademark Office*